US005612353A

United States Patent [19]
Ewing et al.

[11] Patent Number: 5,612,353
[45] Date of Patent: Mar. 18, 1997

[54] SUBSTITUTED (SULFINIC ACID, SULFONIC ACID, SULFONYLAMINO OR SULFINYLAMINO) N-[(AMINOIMINOMETHYL) PHENYLALKYL]-AZAHETEROCYCLYLAMIDE COMPOUNDS

[75] Inventors: William R. Ewing, King of Prussia; Michael R. Becker, Norristown; Henry W. Pauls, Collegeville; Daniel L. Cheney, West Chester, all of Pa.; Jonathan S. Mason, Dagenham, United Kingdom; Alfred P. Spada, Lansdale, Pa.

[73] Assignee: Rhone-Poulenc Rorer Pharmaceuticals Inc., Collegeville, Pa.

[21] Appl. No.: 481,024

[22] Filed: Jun. 7, 1995

[51] Int. Cl.[6] .................. C07D 401/02; A61K 31/40; A61K 31/435

[52] U.S. Cl. .................. 514/309; 514/212; 514/307; 514/329; 514/343; 514/422; 514/426; 540/606; 546/139; 546/141; 546/223; 546/276.4; 548/527; 548/557

[58] Field of Search .................. 540/606; 546/141, 546/223, 281, 139, 276.4; 548/527, 557; 514/212, 307, 309, 343, 329, 422, 426

[56] References Cited

PUBLICATIONS

Chemical Abstract, vol. 119, No. 3, Abstract 28,019n, p. 861, Jul. 19, 1993.

*Primary Examiner*—Zinna Northington Davis
*Attorney, Agent, or Firm*—Raymond S. Parker, III; Martin F. Savitzky; James A. Nicholson

[57] ABSTRACT

The compounds of formula I exhibit useful pharmacological activity and accordingly are incorporated into pharmaceutical compositions and used in the treatment of patients suffering from certain medical disorders. More especially, they are Factor Xa inhibitors. The present invention is directed to compounds of formula I, compositions containing compounds of formula I, and their use, which are for treating a patient suffering from, or subject to, conditions which can be ameliorated by the administration of an inhibitor of Factor Xa.

12 Claims, No Drawings

SUBSTITUTED (SULFINIC ACID, SULFONIC ACID, SULFONYLAMINO OR SULFINYLAMINO) N-[(AMINOIMINOMETHYL)PHENYLALKYL]-AZAHETEROCYCLYLAMIDE COMPOUNDS

FIELD OF THE INVENTION

The compounds of formula I exhibit useful pharmacological activity and accordingly are incorporated into pharmaceutical compositions and used in the treatment of patients suffering from certain medical disorders. More especially, they are Factor Xa inhibitors. The present invention is directed to compounds of formula I, compositions containing compounds of formula I, and their use, which are for treating a patient suffering from, or subject to, conditions which can be ameliorated by the administration of an inhibitor of Factor Xa.

Factor Xa is the penultimate enzyme in the coagulation cascade rather than thrombin. Both free factor Xa and factor Xa assembled in the prothrombinase complex (Factor Xa, Factor Va, calcium and phospholipid) are inhibited. Factor Xa inhibition is obtained by direct complex formation between the inhibitor and the enzyme and is therefore independent of the plasma co-factor antithrombin III. Effective factor Xa inhibition is achieved by administering the compounds either by oral administration, continuous intravenous infusion, bolus intravenous administration or any other parenteral route such that it achieves the desired effect of preventing the factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening thrombin throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

SUMMARY OF THE INVENTION

This invention is directed to the pharmaceutical use of a compound of formula I below to inhibit the production or physiological effects of Factor Xa in the treatment of a patient suffering from a disease state associated with a physiologically detrimental excess of Factor Xa, where formula I is as follows:

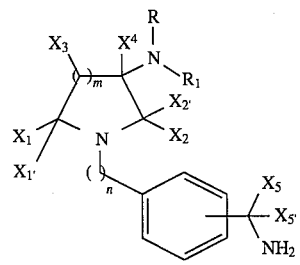

$X_1$ and $X_{1'}$ are hydrogen;

$X_2$ and $X_{2'}$ are independently selected from the group of hydrogen, alkyl, aryl, aralkyl, carboxyalkyl, alkoxycarbonylalkyl or hydroxyalkyl, or $X_1$ and $X_{1'}$ or $X_2$ and $X_{2'}$ independently taken together form oxo;

$X_3$ is hydroxy, alkyl, aralkyl or aryl, or $X_3$ and one of $X_1$ and $X_{1'}$ taken together form a 4 to 7 membered ring;

$X_4$ is hydrogen, alkyl, aralkyl, or hydroxyalkyl;

$X_5$ and $X_{5'}$ are hydrogen or taken together are =NH;

m is 1, 2 or 3;

n is 1, 2 or 3;

R is hydrogen, alkyl, alkylaryl, hydroxyalkyl or alkoxy;

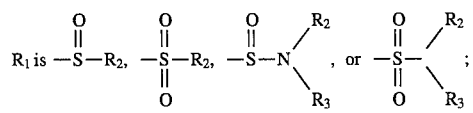

$R_2$ is alkyl, aralkyl, cycloalkyl, aryl, substituted aryl, heterocyclyl aryl, heteroaryl, substituted heteroaryl, hetereocyclyl (thiophene, pyrrole, indole, benzothiophene, phenyl thiophene), tetrahydroisoquinoline, tetrahydroquinoline, indane, tetrahydronapthalene or napthyrdyl, or R and $R_2$ taken together form a 5 to 7 membered ring; and $R_3$ is alkyl, cycloalkyl or aryl, or $R_2$ and $R_3$ taken together form a 4 to 7 membered ring, or a pharmaceutically acceptable salt thereof, an N-oxide thereof, a hydrate thereof or a solvate thereof.

DETAILED DESCRIPTION OF THE INVENTION

As used above, and throughout the description of the invention, the following terms, unless otherwise indicated, shall be understood to have the following meanings:

Definitions

"Patient" includes both human and other mammals.

"Alkyl" means an aliphatic hydrocarbon group which may be straight or branched having about 1 to about 15 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. The alkyl group may be substituted by one or more halo, cycloalkyl or cycloalkenyl. Exemplary alkyl groups include methyl, fluoromethyl, difluoromethyl. trifluoromethyl, cyclopropylmethyl, cyclopentylmethyl, ethyl, n-propyl, i-propyl, n-butyl, t-butyl, n-pentyl, 3-pentyl, heptyl, octyl, nonyl, decyl and dodecyl.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain which may be straight or branched. The alkenyl group may be substituted by one or more halo. Exemplary alkenyl groups include ethenyl, propenyl, n-butenyl, i-butenyl, 3-methylbut-2-enyl, n-pentenyl, heptenyl, octenyl and decenyl.

"Cycloalkyl" means a non-aromatic mono- or multicyclic ring system of about 3 to about 10 carbon atoms. Preferred monocyclic cycloalkyl rings include cyclopentyl, fluorocyclopentyl, cyclohexyl and cycloheptyl; more preferred is cyclopentyl. The cycloalkyl group may be substituted by one or more halo, methylene ($H_2C=$) or alkyl. Exemplary multicyclic cycloalkyl rings include 1-decalin, adamant-(1- or 2-)yl and norbornyl.

"Cycloalkenyl" means a non-aromatic monocyclic or multicyclic ring system containing a carbon-carbon double bond and having about 3 to about 10 carbon atoms. Preferred monocyclic cycloalkenyl rings include cyclopentenyl, cyclohexenyl or cycloheptenyl; more preferred is cyclopentenyl. A preferred multicyclic cycloalkenyl ring is norbornylenyl. The cycloalkenyl group may be substituted by one or more halo, methylene ($H_2C=$) or alkyl.

"Heterocylyl" means a non-aromatic monocyclic or multicyclic ring system of about 3 to about 10 ring atoms. Preferred rings include about 5 to about 6 ring atoms wherein one of the ring atoms is oxygen, nitrogen or sulfur. The heterocyclyl may be optionally substituted by one or more halo. Preferred monocyclic cyclothioalkyl rings include pyrrole, tetrahydrothiophenyl and tetrahydrothiopyranyl. The thio or nitrogen moiety of the hetercyclyl may also be optionally oxidized to the corresponding N-oxide, S-oxide or S,S-dioxide.

"Aryl" means aromatic carbocyclic radical containing about 6 to about 10 carbon atoms. Exemplary aryl include phenyl or naphthyl, or phenyl or naphthyl substituted with one or more aryl group substituents which may be the same or different, where "aryl group substituent" includes hydrogen, alkyl, aryl, aralkyl, hydroxy, hydroxyalkyl, alkoxy, aryloxy, aralkoxy, carboxy, acyl, aroyl, halo, nitro, cyano, carboxy, alkoxycarbonyl, aryloxycarbonyl, aralkoxycarbonyl, acylamino, aroylamino, alkylsulfonyl, arylsulfonyl, alkylsulfinyl, arylsulfinyl, alkylthio, arylthio, aralkylthio, $Y^1Y^2N-$, $Y^1Y^2NCO-$ or $Y^1Y^2NSO_2-$, where $Y^1$ and $Y^2$ are independently hydrogen, alkyl, aryl, and aralkyl. Preferred aryl group substituents include hydrogen, alkyl, hydroxy, acyl, aroyl, halo, nitro, cyano, alkoxycarbonyl, acylamino, alkylthio, $Y^1Y^2N-$, $Y^1Y^2NCO-$ or $Y^1Y^2NSO_2-$, where $Y^1$ and $Y^2$ are independently hydrogen and alkyl.

"Heteroaryl" means about a 5- to about a 10- membered aromatic monocyclic or multicyclic hydrocarbon ring system in which one or more of the carbon atoms in the ring system is/are element(s) other than carbon, for example nitrogen, oxygen or sulfur. The "heteroaryl" may also be substituted by one or more aryl group substituents. Exemplary heteroaryl groups include pyrazinyl, furanyl, thienyl, pyridyl, pyrimidinyl, isoxazolyl, isothiazolyl, quinolinyl, and isoquinolinyl. Preferred heteroaryl groups include pyrazinyl, thienyl, pyridyl, pyrimidinyl, isoxazolyl and isothiazolyl.

Aryl, Heteroaryl, cycloalkyl and heterocyclyl may be fused together and are included in the definition of $R_2$.

"Aralkyl" means an aryl-alkyl- group in which the aryl and alkyl are as previously described. Preferred aralkyls contain a lower alkyl moiety. Exemplary aralkyl groups include benzyl, 2-phenethyl and naphthlenemethyl.

"Hydroxyalkyl" means a HO-alkyl- group in which alkyl is as previously defined. Preferred hydroxyalkyls contain lower alkyl. Exemplary hydroxyalkyl groups include hydroxymethyl and 2-hydroxyethyl.

"Acyl" means an H—CO— or alkyl-CO— group in which the alkyl group is as previously described. Preferred acyls contain a lower alkyl. Exemplary acyl groups include formyl, acetyl. propanoyl, 2-methylpropanoyl, butanoyl and palmitoyl.

"Aroyl" means an aryl-CO— group in which the alkyl group is as previously described. Exemplary groups include benzoyl and 1- and 2-naphthoyl.

"Alkoxy" means an alkyl-O— group in which the alkyl group is as previously described. Exemplary alkoxy groups include methoxy, ethoxy, n-propoxy, i-propoxy, n-butoxy and heptoxy.

"Aryloxy" means an aryl-O— group in which the aryl group is as previously described. Exemplary aryloxy groups include phenoxy and naphthoxy.

"Aralkyloxy" means an aralkyl-O— group in which the aralkyl groups is as previously described. Exemplary aralkyloxy groups include benzyloxy and 1- or 2-naphthalenemethoxy.

"Alkylthio" means an alkyl-S— group in which the alkyl group is as previously described. Exemplary alkylthio groups include methylthio, ethylthio, i-propylthio and heptylthio.

"Arylthio" means an aryl-S— group in which the aryl group is as previously described. Exemplary arylthio groups include phenylthio and naphthylthio.

"Aralkylthio" means an aralkyl-S— group in which the aralkyl group is as previously described. An exemplary aralkylthio group is benzylthio.

"$Y^1Y^2N-$" means a substituted or unsubstituted amino group, wherein $Y^1$ and $Y^2$ are as previously described. Exemplary groups include amino ($H_2N-$), methylamino, ethylmethylamino, dimethylamino and diethylamino.

"Alkoxycarbonyl" means an alkyl-O—CO— group. Exemplary alkoxycarbonyl groups include methoxy- and ethoxycarbonyl.

"Aryloxycarbonyl" means an aryl-O—CO— group. Exemplary aryloxycarbonyl groups include phenoxy- and naphthoxycarbonyl.

"Aralkoxycarbonyl" means an aralkyl-O—CO— group. An exemplary aralkoxycarbonyl group is benzyloxycarbonyl.

"$Y^1Y^2NCO-$" means a substituted or unsubstituted carbamoyl group, wherein $Y^1$ and $Y^2$ are as previously described. Exemplary groups are carbamoyl ($H_2NCO-$) and dimethylaminocarbamoyl ($Me_2NCO-$).

"$Y^1Y^2NSO_2-$" means a substituted or unsubstituted sulfamoyl group, wherein $Y^1$ and $Y^2$ are as previously described. Exemplary groups are aminosulfamoyl ($H_2NSO_2-$) and dimethylaminosulfamoyl ($Me_2NSO_2-$).

"Acylamino" is an acyl-NH— group wherein acyl is as defined herein.

"Aroylamino" is an aroyl-NH— group wherein aroyl is as defined herein.

"Alkylsulfonyl" means an alkyl-$SO_2-$ group. Preferred groups are those in which the alkyl group is lower alkyl.

"Alkylsulfinyl" means an alkyl-SO— group. Preferred groups are those in which the alkyl group is lower alkyl.

"Arylsulfonyl" means an aryl-SO$_2$— group.

"Arylsulfinyl" means an aryl-SO— group.

"Halo" means fluoro, chloro, bromo, or iodo. Preferred are fluoro, chloro or bromo, and more preferred are fluoro or chloro.

Preferred Embodiments

A preferred embodiment of the invention is a method for treating a disease state capable of being modulated by inhibiting production of Factor Xa to a patient suffering from said disease state an effective amount of the compound of formula I.

A preferred compound aspect of the invention is the compound of formula I wherein $R_2$ is biphenyl, substituted biphenyl, naphthyl or substituted naphthyl.

Another preferred compound aspect of the invention is the compound of formula I wherein n is 1.

Another preferred compound aspect of the invention is the compound of formula I wherein $X_2$ and $X_{2'}$ are oxo.

Another preferred compound aspect of the invention is the compound of formula I wherein $X_1$, $X_{1'}$, $X_3$ and $X_4$ are hydrogen.

Another preferred compound aspect of the invention is the compound of formula I $X_5$ is hydrogen or alkyl.

Another preferred compound aspect of the invention is the compound of formula I wherein aminoiminomethyl on the N-phenylalkyl is in the meta position.

Another preferred compound aspect of the invention is the compound of formula I $X_1$ is hydrogen and $X_{1'}$ is carboxyalkyl, alkoxycarbonylalkyl or aryl, or $X_1$ and $X_{1'}$ taken together form oxo.

Another preferred compound aspect of the invention is the compound of formula I wherein $R_1$ is $SO_2R_2$.

Species according to the invention are selected from the following:

Naphthalene-2-sulfonic acid {1-[3-(aminoiminomethyl)-benzyl]-2-oxo-pyrrolidin-3-(S)-yl}-amide trifluoroacetate;

Dibenzofuran-2-sulfonic acid {1-[3-(aminoiminomethyl)-benzyl]-5-oxo-pyrrolidin-3-yl}-amide trifluoroacetate;

Toluene-4-sulfonic acid {1-[3-(aminoiminomethyl)-benzyl]-2-oxo-pyrrolidin-3-(S)-yl}-amide trifluoroacetate;

3,4-Dihydro-1H-isoquinoline-2-sulfonic acid {1-[3-(aminoiminomethyl)-benzyl]-2-oxo-pyrrolidin-3-(S)-yl}-amide trifluoroacetate;

3'-Methoxy-biphenyl-4-sulfonic acid {1-[3-(aminoiminomethyl)-benzyl]-2-oxo-pyrrolidin-3-(S)-yl}-amide trifluoroacetate;

Naphthalene-1-sulfonic acid {1-[3-(aminoiminomethyl)-benzyl]-2-oxo-pyrrolidin-3-(S)-yl}-amide trifluoroacetate;

5-Pyrid-2-yl-thiophene-2-sulfonic acid {1-[3-(aminoiminomethyl)-benzyl]-2-oxo-pyrrolidin-3-(S)-yl}-amide trifluoroacetate;

Biphenyl-4-sulfonic acid {1-[3-(aminoiminomethyl)-benzyl]-2-oxo-pyrrolidin-3-(S)-yl}-amide trifluoroacetate;

7-Methoxynaphthalene-2-sulfonic acid {1-[3-(aminoiminomethyl)-benzyl]-2-oxo-pyrrolidin-3-(S)-yl}-amide trifluoroacetate;

7-Ethoxynaphthalene-2-sulfonic acid {1-[3-(aminoiminomethyl)-benzyl]-2-oxo-pyrrolidin-3-(S)-yl}-amide trifluoroacetate;

5-Chloro-6-methoxynaphthalene-2-sulfonic acid {1-[3-(aminoiminomethyl)-benzyl]-2-oxo-pyrrolidin-3-(S)-yl}-amide trifluoroacetate;

5-Chloro-6,7-dimethoxynaphthalene-2-sulfonic acid {1-[3-(aminoiminomethyl)-benzyl]-2-oxo-pyrrolidin-3-(S)-yl}-amide trifluoroacetate;

5-Chloro-6,7-dimethoxynaphthalene-2-sulfonic acid {1-[3-(aminoiminomethyl)-benzyl]-2-oxo-pyrrolidin-3-(S)-yl}-amide trifluoroacetate;

7-Aminonaphthalene-2-sulfonic acid {1-[3-(aminoiminomethyl)-benzyl]-2-oxo-pyrrolidin-3-(S)-yl}-amide ditrifluoroacetate;

Naphthalene-2-sulfonic acid {1-[4-(aminoiminomethyl)-benzyl]-2-oxo-pyrrolidin-3-(S)-yl}-amide trifluoroacetate;

7-Methoxynaphthalene-2-sulfonic acid [1-(3-aminomethyl-benzyl)-2-oxo-pyrrolidin-3-(S)-yl]-amide trifluoroacetate;

Naphthalene-2-sulfonic acid {1-[3-(aminoiminomethyl)-benzyl]-2-oxo-pyrrolidin-3-(S)-yl}methyl amide trifluoroacetate;

Naphthalene-2-sulfonic acid {1-[3-(aminoiminomethyl)-benzyl]-pyrrolidin-3-(S)-yl}-amide ditrifluoroacetate;

7-Methoxynaphthalene-2-sulfonic acid {1-[3-(aminoiminomethyl)-benzyl]-2,5-dioxo-pyrrolidin-3-(S)-yl}-amide trifluoroacetate;

Naphthalene-2-sulfonic acid {1-[3-(aminoiminomethyl)-benzyl]-2-oxo-piperidin-3-yl}-amide trifluoroacetate;

7-Methoxynaphthalene-2-sulfonic acid {1-[3-(aminoiminomethyl)-benzyl]-2-oxo-azepan-3-(S)-yl}-amide trifluoroacetate; or 7-Methoxy-naphthalene-2-sulfonic acid {1-[3-(aminoiminomethyl)-benzyl]-2-oxo-pyrrolidin-3-(S)-yl}methyl amide trifluoroacetate.

Preferred compounds for use according to the invention are selected from the following:

Naphthalene-2-sulfonic acid {1-[3-(aminoiminomethyl)-benzyl]-2-oxo-pyrrolidin-3-(S)-yl}-amide trifluoroacetate;

Dibenzofuran-2-sulfonic acid {1-[3-(aminoiminomethyl)-benzyl]-5-oxo-pyrrolidin-3-yl}-amide trifluoroacetate;

Toluene-4-sulfonic acid {1-[3-(aminoiminomethyl)-benzyl]-2-oxo-pyrrolidin-3-(S)-yl}-amide trifluoroacetate;

3,4-Dihydro-1H-isoquinoline-2-sulfonic acid {1-[3-(aminoiminomethyl)-benzyl]-2-oxo-pyrrolidin-3-(S)-yl}-amide trifluoroacetate;

3'-Methoxy-biphenyl-4-sulfonic acid {1-[3-(aminoiminomethyl)-benzyl]-2-oxo-pyrrolidin-3-(S)-yl}-amide trifluoroacetate;

Naphthalene-1-sulfonic acid {1-[3-(aminoiminomethyl)-benzyl]-2-oxo-pyrrolidin-3-(S)-yl}-amide trifluoroacetate;

5-Pyrid-2-yl-thiophene-2-sulfonic acid {1-[3-(aminoiminomethyl)-benzyl]-2-oxo-pyrrolidin-3-(S)-yl}-amide trifluoroacetate;

Biphenyl-4-sulfonic acid {1-[3-(aminoiminomethyl)-benzyl]-2-oxo-pyrrolidin-3-(S)-yl}-amide trifluoroacetate:

7-Methoxynaphthalene-2-sulfonic acid {1-[3-(aminoiminomethyl)-benzyl]-2-oxo-pyrrolidin-3-(S)-yl}-amide trifluoroacetate;

7-Ethoxynaphthalene-2-sulfonic acid {1-[3-(aminoiminomethyl)-benzyl]-2-oxo-pyrrolidin-3-(S)-yl}-amide trifluoroacetate;

5-Chloro-6-methoxynaphthalene-2-sulfonic acid {1-[3-(aminoiminomethyl)-benzyl]-2-oxo-pyrrolidin-3-(S)-yl}-amide trifluoroacetate;

5-Chloro-6,7-dimethoxynaphthalene-2-sulfonic acid {1-[3-(aminoiminomethyl)-benzyl]-2-oxo-pyrrolidin-3-(S)-yl}-amide trifluoroacetate;

5-Chloro-6,7-dimethoxynaphthalene-2-sulfonic acid {1-[3-(aminoiminomethyl)-benzyl]-2-oxo-pyrrolidin-3-(S)-yl}-amide trifluoroacetate;

7-Aminonaphthalene-2-sulfonic acid {1-[3-(aminoiminomethyl)-benzyl]-2-oxo-pyrrolidin-3-(S)-yl}-amide ditrifluoroacetate;

Naphthalene-2-sulfonic acid {1-[4-(aminoiminomethyl)-benzyl]-2-oxo-pyrrolidin-3-(S)-yl}-amide trifluoroacetate;

7-Methoxynaphthalene-2-sulfonic acid [1-(3-aminomethyl-benzyl)-2-oxo-pyrrolidin-3-(S)-yl]-amide trifluoroacetate;

Naphthalene-2-sulfonic acid {1-[3-(aminoiminomethyl)-benzyl]-2-oxo-pyrrolidin-3-(S)-yl}methyl amide trifluoroacetate;

Naphthalene-2-sulfonic acid {1-[3-(aminoiminomethyl)-benzyl]-pyrrolidin-3-(S)-yl}-amide ditrifluoroacetate;

7-Methoxynaphthalene-2-sulfonic acid {1-[3-(aminoiminomethyl)-benzyl]-2,5-dioxo-pyrrolidin-3-(S)-yl}-amide trifluoroacetate;

Naphthalene-2-sulfonic acid {1-[3-(aminoiminomethyl)-benzyl]-2-oxo-pyrrolidin-3-yl}-amide trifluoroacetate;

7-Methoxynaphthalene-2-sulfonic acid {1-[3-(aminoiminomethyl)-benzyl]-2-oxo-azepan-3-(S)-yl}-amide trifluoroacetate; and 7-Methoxy-naphthalene-2-sulfonic acid {1-[3-(aminoiminomethyl)-benzyl]-2-oxo-pyrrolidin-3-(S)-yl}methyl amide trifluoroacetate.

A preferred compound includes

7-Methoxy-naphthalene-2-sulfonic acid {1-[3-(aminoiminomethyl)-benzyl]-2-oxo-pyrrolidin-3-(S)-yl}methyl amide trifluoroacetate Compounds of formula I may be prepared by the application or adaptation of known methods, by which is meant methods used heretofore or described in the literature.

Thus, compounds of formula I

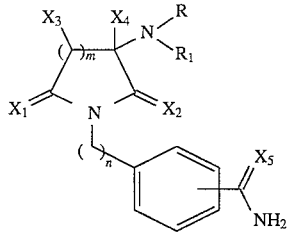

The compounds of formula I of the invention may be prepared as outlined below.

Compounds of formula I in which $X_2=O$ and $X_1 \neq O$ may be prepared starting with an aldehyde or ketone of formula II

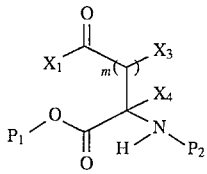

(where $P_1$ is alkyl, alkyl aryl, or aryl and $P_2$ is an alkyl, alkyl aryl, or aryl carbamate by reductive amination using a cyanophenyl alkyl amine of formula III

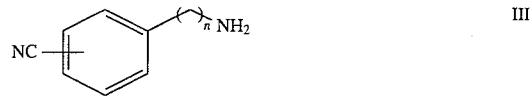

in an alcoholic solvent such as methanol and an imine reducing reagent such as sodium cyanoborohydride, sodium triacetoxyborohydride or catalytic hydrogenation using for example palladium at a temperature between 0° C. to 100° C. to give the cyclic structure represented by formula IV.

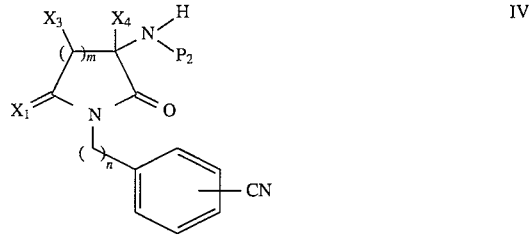

The $P_2$ group is removed by the appropriate deblocking procedures known for carbamates such as strong acid, strong base or catalytic hydrogenation to give compounds of formula V.

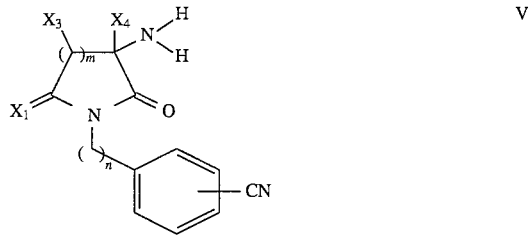

The amine is then coupled to any of the groups represented by formula VI

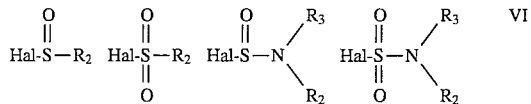

where Hal is a halogen atoms, using an inert solvent such as dichloromethane, tetrahydrofuran, ether at temperatures between 0° to 100° C. in the presence or absence of an activating agent such as dimethyl aminopyridine to give compounds of formula VII.

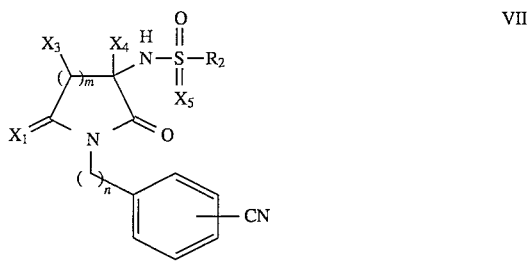

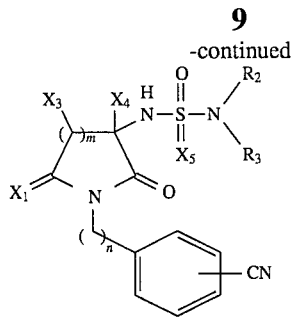
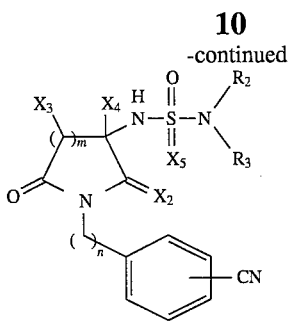

Compounds represented by formula VII can be converted to the corresponding amidine by the use of an alcoholic solvent such as ethanol saturated with hydrogen chloride (gas). The resulting product is then dissolved in an alcoholic solvent such as methanol saturated with ammonia to give compounds of formula I. Alternatively, compounds of formula VII can be dissolved in a solution of pyridine containing a tertiary amine base such as triethyl amine saturated with hydrogen sulfide at a temperature between 0° C. and 60° C. The resulting product is then dissolved in an organic solvent such as acetone and reacted with an alkyl halide such as methyl iodide at a temperature between 0° C. and 80° C. The resulting product is then dissolved in an alcoholic solvent such as methanol and reacted with ammonium acetate to give compounds of formula I. When $X_1=O$ and $X_2 \neq O$, compounds of formula I can be prepared starting with an aldehyde or ketone represented by formula VIII.

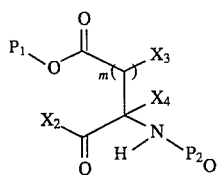

VIII

In an analogous fashion to the preparation of compounds represented by formula V, compounds represented by formula IX are prepared.

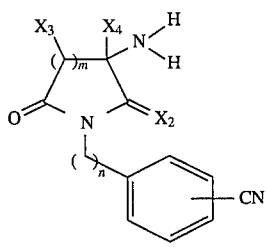

IX

Compounds of formula IX are then converted to compounds represented by formula X in an analogous procedure to that given for the conversion of compounds of formula V to compounds of formula VI.

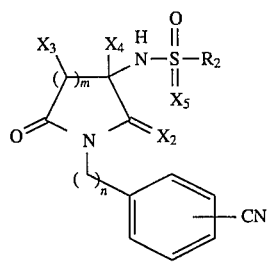

X

An alternative procedure for the conversion of compounds represented by formula V and formula IX to compounds represented by formula I is outlined below. Compounds of formula V or of formula IX are dissolved in an alcoholic solvent such as ethanol saturated with HCl. The resulting product is then dissolved in an alcoholic solvent such as methanol saturated with ammonia to give compounds of formula XI.

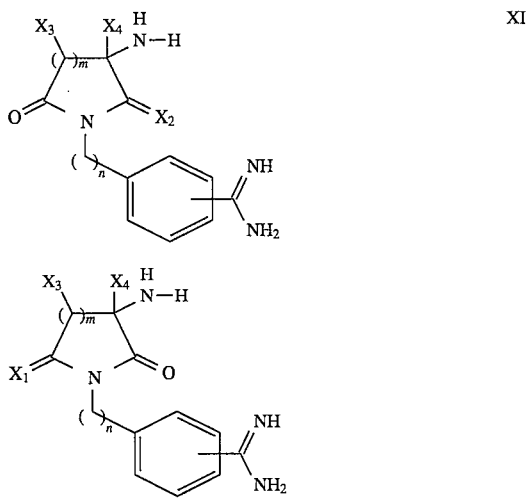

XI

Compounds of formula XI are dissolved in an organic solvent such as ethanol or dimethylformamide and compounds of formula IV are added at a temperature between 0° C. to 100° C. in the presence or absence of an activating reagent such as dimethyl aminopyridine to give compounds represented by formula I.

Alternatively compounds of formula I can be prepared starting with compounds represented by formula XII.

Compounds of formula XII are dissolved in an inert organic solvent such as tetrahydrofuran at a temperature between −78° C. and 25° C.

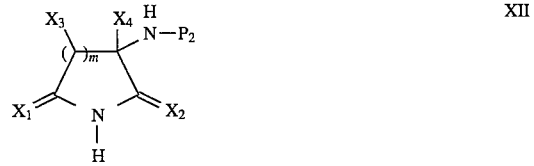

XII

To the solution is added a base such as sodium hydride, lithium hexamethyldisilylazide, or lithium diisopropyl amine. To the solution is then added a compound of formula XIII

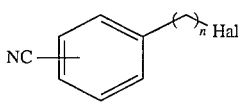

where Hal is a halogen atom to give compounds of formula IV which are then converted to compounds of formula I as described above.

Compounds of formula I in which R≠H are prepared starting with compounds of formula VII or of formula X.

Compounds of formula VII or of formula X are dissolved in an inert organic solvent such as tetrahydrofuran, dioxane, or dimethyl formamide at 0° C. to 100 ° C. To the resulting solution is added a base such as sodium hydride or potassium carbonate and a compound of formula XIV.

R-Hal     XIV where Hal is a halogen.

The product of this preparation is compounds of formula XV.

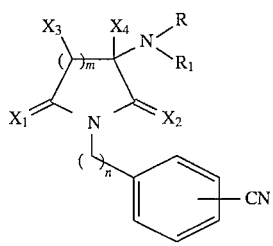

Compounds of formula XV are converted to compounds of formula I as described above.

Compounds of formula I in which $X_5$=H, H are prepared by reduction of compounds represented by formulas VII, X, XV using hydrogenation in an appropriate solvent such as methanol in the presence of a catalyst such as rodium on alumina. This transformation can also be achieved using a hydride reagent such as disobutyl aluminum hydride to give compounds of formula I in which $X_5$=H, H.

Compounds of the present invention may contain asymmetric centers. These asymmetric centers may independently be in either the R or S configuration. It will be apparent to those skilled in the art that certain compounds of the invention may also exhibit geometrical isomerism. The present invention comprises the individual geometrical isomers and stereoisomers and mixtures thereof.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

The compounds of the present invention are useful in the form of the free base or acid or in the form of a pharmaceutically acceptable salt thereof. All forms are within the scope of the invention.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects on Factor Xa inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrohalides, e.g. hydrochloride and hydrobromide, sulfate, phosphate, nitrate, sulfamate, acetate, citrate, lactate, tartarate, malonate, oxalate, salicylate, propionate, succinate, fumarate, maleate, methylene-bis-B-hydroxynaphthoates, gentisates, mesylates, isethionates and di-p-toluoyltartratesmethanesulfonate, ethanesulfonate, benzenesulfonate, p-toluenesulfonate, cyclohexylsulfamate and quinate, respectively.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are nontoxic to the animal organism in pharmaceutical doses of the salts, so that the beneficial inhibitory effects on Factor Xa inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The base addition salts of the compounds of this invention can be regenerated from the salts by the application or adaptation of known methods. For example, parent compounds of the invention can be regenerated from their base addition salts by treatment with an acid, e.g. hydrochloric acid.

As will be self-evident to those skilled in the art, some of the compounds of this invention do not form stable salts. However, acid addition salts are most likely to be formed by compounds of this invention having a nitrogen-containing heteroaryl group and/or wherein the compounds contain an amino group as a substituent. Preferable acid addition salts of the compounds of the invention are those wherein there is not an acid labile group.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

It will be apparent to those skilled in the art that certain compounds of formula I can exhibit isomerism, for example geometrical isomerism and optical isomerism. Geometrical isomers include the cis and trans forms of compounds of the invention having alkenyl or diazenyl moieties. All isomers within formula I, and their mixtures, are within the scope of the invention.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

The starting materials and intermediates are prepared by the application or adaptation of known methods, for example methods as described in the Reference Examples or their obvious chemical equivalents.

The present invention is further exemplified but not limited by the following illustrative examples which illustrate the preparation of the compounds according to the invention. The Reference Examples illustrate the preparation of the intermediates.

In the nuclear magnetic resonance spectra (NMR) the chemical shifts are expressed in ppm relative to tetramethylsilane. Abbreviations have the following significance: s=singlet; d=doublet; t=triplet; m=multiplet; dd=doublet of doublets; ddd=doublet of doublets of doublets; dt=doublet of triplets, b=broad.

EXAMPLE 1

Naphthalene-2-sulfonic acid {1-[3-(aminoiminomethyl)-benzyl]-2-oxo-pyrrolidin-3-(S)-yl}-amide trifluoroacetate.

A. Boc-L-Asp(H)-OBn.

Boc-L-Asp-OBn (15 g, 46.4 mmol) is dissolved in 50 mL of THF and cooled to −10° C. The solution is treated with N-methylmorpholine (4.9 g, 48.7 mmol) and stirred for 5 minutes. To the solution is added dropwise isobutyl chloroformate (6.3 g, 46.4 mmol). After the addition is completed, the solution is stirred for 1 minutes, then filtered through a pad of Celite. The collected solution is cooled to −10° C. To the solution is added sodium borohydride (2.63 g, 70 mmol) predissolved in 50 mL of water. The solution is stirred for 2 minutes. The solution is poured into a separatory funnel and diluted with 800 mL of EtOAc. The organic layer is washed with water and saturated NaCl. The organic layer is dried over $MgSO_4$, filtered and concentrated. The resulting residue is added to a solution of oxalyl chloride (30 mL of a 2M solution in $CH_2Cl_2$, 60 mmol), and methyl sulfoxide (7.25 g, 92.8 mmol) in 250 mL of $CH_2Cl_2$ at −78° C. The reaction mixture is stirred at −78° C. for 40 minutes, then triethylamine (14 g, 140 mmol) is added. The reaction mixture is stirred at −78° C. for 1 hour and then is stirred at room temperature for 30 minutes. The solution is poured into 200 mL of a 20% citric acid/water solution. The resulting mixture is poured into a separatory funnel and the layers are separated. The organic layer is washed with water and saturated NaCl. The organic layer is dried over $MgSO_4$, filtered and concentrated. The residue is purified by column chromatography eluting with a gradient of 10% EtOAc/hexanes to 30% EtOAc/hexanes. The product aldehyde (12.0 g, 39.0 mmol) is obtained as an oil.

$^1$H NMR (CDCl$_3$, 300 MHz) d 9.68 (s, 1H), 7.32 (m, 4H), 5.42 (bs, 1H), 5.16 (s, 2H), 4.62 (m, 2H), 3.05 (ddd, 2H), 1.40 (s, 9H).

B. [1-(3-Cyanobenzyl)-2-oxo-pyrrolidin-3-(S)-yl]-carbamic acid tert-butyl ester.

To a solution of Boc-L-Asp(H)-OBn (13.5 g, 44 mmol) dissolved in 75 mL of methanol is added m-cyanobenzylamine hydrochloride (7.4 g, 44 mmol) and triethylamine (4.7 g, 46 mmol). The solution is stirred for 30 minutes. After this time, a solution of sodium cyanoborohydride (3.0 g, 48.4 mmol) and zinc chloride (3.3 g, 24.2 mmol) in 30 mL of MeOH is added. The mixture is stirred for an additional 2 hours. After this time, 20 mL of 1N NaOH and 100 mL of water is added, and the resulting mixture is concentrated. The residue is treated with 100 mL of water and 800 mL of EtOAc. The solution is filtered through a pad of Celite, poured into a separatory funnel and the layers are separated. The organic layer is washed with 1N HCl, 10% $Na_2CO_3$ and saturated NaCl. The organic layer is dried over $MgSO_4$, filtered and concentrated. The residue is purified by column chromatography eluting with a gradient of 20% EtOAc/$CH_2Cl_2$ to 40% EtOAc/$CH_2Cl_2$ to give the title compound (9.1 g, 29 mmol) as a white solid.

$^1$H NMR (CDCl$_3$, 300 MHz) d 7.55 (m, 4H), 5.18 (bs, 1H), 4.47 (AB, 2H), 4.18 (dd, 1H), 3.21 (m, 2H), 2.60 (m, 1H), 1.88 (m, 1H), 1.42 (s, 9H).

C. 3-(3-(S)-Amino-2-oxo-pyrrolidin-1-ylmethyl)-benzonitrile hydrochloride.

To a solution of [1-(3-cyanobenzyl)-2-oxo-pyrrolidin-3-(S)-yl]-carbamic acid tert-butyl ester (9.1 g, 29 mmol) in 150 mL of EtOAc at 0° C. is bubbled HCl gas for 10 minutes. After this time, the solution is stirred for 4 hours. The solution is then concentrated to give the title compound (7.3 g, 29 mmol) as a white solid.

$^1$H NMR (DMSO-d$_6$, 300 MHz) d 8.71 (bs, 3H), 7.85 (m, 2H), 7.70 (m, 2H), 4.58 (AB, 2H), 4.13 (m, 1H), 3.32 (m, 2H), 2.44 (m, 1H), 2.18 (m, 1H).

D. Naphthalene-2-Sulfonic acid [1-(3-Cyanobenzyl)-2-oxo-pyrrolidin-3-(S)-yl]-amide.

3-(3-(S)-Amino-2-oxo-pyrrolidin-1-ylmethyl)-benzonitrile hydrochloride (0.40 g, 1.6 mmol) is suspended in 10 mL of $CH_2Cl_2$. To the solution is added triethylamine (0.49 g, 4.8 mmol) followed by 2-naphthalene sulfonyl chloride (0.40 g, 1.8 mmol). After stirring for 2 h, the solution is diluted with $CH_2Cl_2$.

The solution is washed with 1N HCl, 10% $Na_2CO_3$ and saturated NaCl. The organic layer is dried over $MgSO_4$, filtered and concentrated. The residue is triturated with ether to give the title compound (0.46 g, 1.13 mmol) as a solid.

$^1$H NMR (DMSO-$d_6$, 300 MHz) d 8.56 (d, 1H), 8.32 (d, 1H), 8.20 (m, 3H), 8.09 (m, 1H), 7.93 (d, 1H), 7.74 (m, 3H), 7.48 (d, 2H), 4.38 (AB, 2H), 4.17 (m, 1H), 3.05 (m, 2H), 2.02 (m, 1H), 1.57 (m, 1H).

E. Naphthalene-2-sulfonic acid {1-[3-(aminoiminomethyl)-benzyl]-2-oxo-pyrrolidin-3-yl}-amide trifluoroacetate.

Naphthalene-2-sulfonic acid [1-(3-cyanobenzyl)-2-oxo-pyrrolidin-3-(S)-yl]-amide (0.46 g, 1.13 mmol) is dissolved in 50 mL of ethanol. The solution is cooled to 0° C. and HCl gas is bubbled through the solution for 10 minutes. The ice bath is removed and the reaction mixture is stirred at room temperature for 6 hours. After this time, the solution is concentrated. The residue is dissolved in 50 mL of methanol. The solution is cooled to 0° C. and ammonia gas is bubbled through the solution for 10 minutes. The reaction mixture is stirred for 24 hours. After this time, the solution is concentrated. The residue is purified by RP-HPLC eluting with a gradient of 10% $CH_3CN/H_2O$ (0.1% TFA) to 60% $CH_3CN/H_2O$ (0.1% TFA). The appropriate fractions are lyophilized to give the title compound (0.33 g, 0.61 mmol) as a solid.

$^1$H NMR (DMSO-$d_6$, 300 MHz) d 9.30 (bs, 2H), 9.14 (bs, 2H), 8.50 (s, 1H), 8.28 (d, 1H), 8.13 (m, 3H), 8.04 (d, 1H), 7.91 (d, 1H), 7.80 (m, 3H), 7.62 (d, 2H), 4.42 (AB, 2H), 4.18 (m, 1H), 3.10 (m, 2H), 2.00 (m, 1H), 1.57 (m, 1H). FAB MS, [M+H]$^+$=423. Elemental analysis calculated with 1.5 mole of $H_2O$: C=51.15%, H=4.65%, N=9.94%, found C=51.16%, H=4.19%, N=9.61%.

EXAMPLE 2

Dibenzofuran-2-sulfonic acid {1-[3-(aminoiminomethyl)-benzyl]-5-oxo-pyrrolidin-3-yl}-amide trifluoroacetate.

A. Boc-Asp(OBn)-H.

The title compound is prepared as in EXAMPLE 1, Part A, using Boc-Asp(OBn)-OH in place of Boc-L-Asp-OBn.

$^1$H NMR (CDCl$_3$, 300 MHz) d 9.67 (s, 1H), 7.32 (m, 5H), 5.60 (bs, 1H), 5.12 (AB, 2H), 4.40 (m, 1H), 3.94 (AB, 1H), 3.72 (AB, 1H), 1.41 (s, 9H).

B. [1-(3-Cyanobenzyl)-5-oxo-pyrrolidin-3-yl]-carbamic acid tert-butyl ester.

The title compound is prepared as in EXAMPLE 1, Part B using Boc-Asp(OBn)-H in place of Boc-Asp(H)-OBn.

$^1$H NMR (CDCl$_3$, 300 MHz) d 7.65 (d, 1H), 7.61 (s, 1H), 7.52 (m, 2H), 4.82 (bs, 1H), 4.51 (s, 2H), 4.22 (m, 1H), 3.53(q, 1H), 3.16(dd, 1H),2.83 (AB, 1H), 2.33 (AB, 1H), 1.40 (s, 9H).

C. 3.-(3-Amino-5-oxo-pyrrolidin-1-ylmethyl)-benzonitrile hydrochloride,

The title compound is prepared as in EXAMPLE 1, Part C using [1-(3-cyanobenzyl)-5-oxo-pyrrolidin-3-yl]-carbamic acid tert-butyl ester in place of [1-(3-cyanobenzyl)-2-oxo-pyrrolidin-3-(S)-yl]-carbamic acid tert-butyl ester.

$^1$H NMR (DMSO-$d_6$, 300 MHz) d 8.5 (bs, 3H), 7.72 (m, 2H), 7.61 (m, 1H), 7.55 (m, 1H), 4.46 (AB, 2H), 3.89 (m, 1H), 3.57 (q, 1H), 3.30 (dd, 1H), 2.78 (AB, 1H), 2.42 (AB, 1H).

D. Dibenzofuran-2-Sulfonic acid [1-(3-cyanobenzyl)-5-oxo-pyrrolidin-3-yl]-amide.

The title compound is prepared from 3-(3-amino-5-oxo-pyrrolidin-1-ylmethyl)benzonitrile hydrochloride as in EXAMPLE 1, Part D using 2-dibenzofuransulfonyl chloride in place of 2-naphthalene sulfonyl chloride. The crude product is purified by column chromatography in a gradient of $CH_2Cl_2$ to 5% MeOH/$CH_2Cl_2$.

$^1$H NMR (CDCl$_3$, 300 MHz) d 8.45 (d, 1H), 7.91 (m, 2H), 7.61 (m, 2H), 7.58 (d, 1H), 7.44 (m, 5H), 5.55 (m, 1H), 4.42 (AB, 2H), 4.09 (m, 1H), 3.50 (dd, 1H), 3.21 (dd, 1H), 2.62 (dd, 1H), 2.29 (dd, 1H).

E. Dibenzofuran-2-sulfonic acid {1-[3-(aminoiminomethyl)-benzyl]-5-oxo-pyrrolidin-3-yl}-amide trifluoroacetate.

Hydrogen sulfide gas is bubbled through a solution of dibenzofuran-2-sulfonic acid [1-(3-cyanobenzyl)-5-oxo-pyrrolidin-3-yl]-amide (0.44 g, 0.99 mmol)in 10 mL of 10:1 pyridine/triethylamine. After stirring the pale green solution for a period of 18 h, the reaction mixture is concentrated in vacuo. The residue is diluted in EtOAc and 0.5N HCl solution. The layers are separated and the organic phase is washed with saturated NaCl. The organic layer is dried over anhydrous $MgSO_4$, filtered and concentrated to give crude thioamide. To a solution of thioamide in 20 mL of acetone is added iodomethane (2.0 mL, 32.0 mmol). The resulting mixture is heated at reflux for 1 h, allowed to cool to room temperature and concentrated in vacuo to provide the crude thioimidate hydroiodide. To a solution of thioimidate hydroiodide in 20 mL of MeOH is added ammonium acetate (0.30 g, 3.89 mmol). The resulting mixture is heated at reflux for 3.5 h, allowed to cool to room temperature and concentrated in vacuo to provide the crude amidine salt. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound (0.21 g, 0.36 mmol) as a white solid.

$^1$H NMR (DMSO-$d_6$, 300 MHz) d 9.29 (s, 4H), 8.64 (s, 1H), 8.24 (d, 1H), 8.13 (d, 1H), 7.91 (m, 2H), 7.84 (d, 1H), 7.60 (m, 6H), 4.39 (AB, 2H), 3.91 (m, 1H), 3.41 (dd, 1H), 3.08 (m, 1H), 2.46 (dd, 1H), 2.13 (dd, 1H). FAB MS, [M+H]$^+$=463. Elemental analysis calculated with 2.3 mole of $H_2O$: C=50.50%, H=4.51%, N=9.06%; found C=50.49%, H=3.66%, N=8.61%.

EXAMPLE 3

Toluene 4-sulfonic acid {1-[3-(aminoiminomethyl)-benzyl]-2-oxo-pyrrolidin-3-(S)-yl}-amide trifluoroacetate.

A. Toluene-4-sulfonic acid [1-(3-cyanobenzyl)-2-oxo-pyrrolidin-3-(S)-yl]-amide.

The title compound is prepared as in EXAMPLE 1, Part D using toluene sulfonyl chloride in place of 2-naphthalene sulfonyl chloride.

$^1$H NMR (DMSO-$d_6$, 300 MHz) d 8.08 (d, 1H), 7.78 (m, 3H), 7.62 (s, 1H), 7.51 (d, 2H), 7.33 (d, 2H), 4.40 (AB, 2H), 4.05 (m, 1H), 3.05 (m, 2H), 2.36 (s, 3H), 1.97 (m, 1H), 1.57 (m, 1H).

B. Toluene-4-sulfonic acid {1-[3-(aminoiminomethyl)-benzyl]-2-oxo-pyrrolidin-3-(S)-yl}-amide trifluoroacetate.

The title compound is prepared as in EXAMPLE 1, Part E using toluene-4-sulfonic acid [1[3-(cyanobenzyl)-2-oxo-pyrrolidin-3-(S)-yl]-amide as the starting material.

$^1$H NMR (DMSO-$d_6$, 300 MHz) d 9.27 (bs, 2H), 9.10 (bs, 2H), 8.03 (d, 1H), 7.79 (d, 2H), 7.68 (m, 1H), 7.59 (m, 4H), 7.40 (d, 2H), 4.44 (AB, 2H), 4.12 (m, 1H), 3.08 (m, 1H), 2.38 (s, 3H), 2.04 (m, 1H), 1.58, (m, 1H). FAB MS, [M+H]$^+$=355. Elemental analysis calculated with 1.25 mole of $H_2O$: C=48.23%, H=4.59%, N=10.39%, found C=48.15%, H=4.59%, N=10.39%.

EXAMPLE 4

3,4-Dihydro-1H-isoquinoline-2-sulfonic acid {1-[3-(aminoiminomethyl)-benzyl]-2-oxo-pyrrolidin-3-(S)-yl}-amide trifluoroacetate.

A. 3,4-Dihydro-1H-isoquinoline-2-sulfonic acid [1-(3-cyanobenzyl)-2-oxo-pyrrolidin-3-(S)-yl]-amide.

A 1M solution of sulfuryl chloride (14.1 mL, 14.1 mmol) in $CH_2Cl_2$ is cooled to 0° C. To the solution is added triethylamine (0.71 g, 7.1 mmol) dropwise. 1,2,3,4-Tetrahydroisoquinoline (0.94 g, 7.1 mmol) is then added dropwise. The ice bath is removed and the solution is stirred for 2 hours. The solution is diluted with $CH_2Cl_2$ and poured into an ice bath. The layers are separated. The organic layer is washed with 1N HCl and saturated NaCl. The organic layer is dried over $MgSO_4$, filtered and concentrated. To the crude residue dissolved in 10 mL of $CH_2Cl_2$ is added 3-(3-(S)-amino-2-oxo-pyrrolidin-1-ylmethyl)-benzonitrile hydrochloride (0.5 g, 2.0 mmol). Triethylamine (0.4 g, 4.0 mmol) is added and the mixture is stirred for 16 hours. The reaction mixture is diluted with EtOAc and washed with 1N HCl, 10% $Na_2CO_3$ and saturated NaCl. The residue is purified by column chromatography eluting with a gradient of 10% EtOAc/$CH_2Cl_2$ to 15% EtOAc/$CH_2Cl_2$ to give the title compound (0.15 g, 0.36 mmol) as a solid.

$^1$H NMR ($CDCl_3$, 300 MHz) d 7.62 (m, 1H), 7.62 (s, 1H), 7.58 (d, 2H), 7.18 (m, 4H), 7.09 (m, 2H), 5.10 (bs, 1H), 4.46 (AB, 2H), 4.08 (m, 1H), 3.65 (m, 2H), 3.22 (m, 2H), 3.02 (m, 2H), 2.61 (m, 1H), 2.05 (m, 1H). FAB MS, $[M+H]^+$=411.

B. 3,4-Dihydro-1H-isoquinoline-2-sulfonic acid {1-[3-(aminoiminomethyl)-benzyl]-2-oxo-pyrrolidin-3-(S)-yl}-amide trifluoroacetate.

The title compound is prepared as described in EXAMPLE 1, Part E using 3,4-dihydro-1H-isoquinoline-2-sulfonic acid [1-(3-cyanobenzyl)-2-oxo-pyrrolidin-3-(S)-yl]-amide as the starting material.

$^1$H NMR (DMSO-$d_6$, 300 MHz) d 9.29 (bs, 2H), 9.13 (bs, 2H), 7.86 (d, 1H), 7.66 (m, 2H), 7.52 (m, 2H), 7.14 (m, 4H), 4.47 (AB, 2H), 4.33 (AB, 2H), 4.12 (m, 1H), 3.43 (m, 2H), 3.18 (m, 2H), 2.88 (m, 2H), 2.30 (m, 1H), 1.77 (m, 1H); FAB MS, $[M+H]^+$=428. Elemental analysis calculated with 2.0 mole of $H_2O$: C=47.83%, H=5.24%, N=12.13%, found C=47.43%, H=4.88%, N=11.63%.

EXAMPLE 5

3'-Methoxy-biphenyl-4-sulfonic acid {1-[3-(aminoiminomethyl)-benzyl]-2-oxo-pyrrolidin-3-(S)-yl}-amide trifluoroacetate.

A. 3'-Methoxy-biphenyl-4-bromide.

3-Bromoanisole (3.5 g, 18.7 mmol) is dissolved in 40 mL of THF and cooled to −78° C. To the solution is added dropwise a 2.5M solution of n-butyllithium in hexanes (7.5 mL, 18.7 mmol). After 10 minutes, a solution of zinc chloride (20 mL, 19.6 mmol) in ether is added and the cooling bath is removed. The reaction mixture is stirred at room temperature for 2 hours. After this time, a solution of 4-iodobromobenzene (5.6 g, 19.6 mmol) and $Pd(Ph_3P)_4$ (1.1 g, 1.0 mmol) in 10 mL of THF is added to the reaction flask. The solution is stirred 2 h, poured into 100 mL of water and extracted with EtOAc. The organic layer is washed with water and saturated NaCl. The organic layer is dried over $MgSO_4$, filtered and concentrated. The crude residue is purified by column chromatography eluting with 10% $CH_2Cl_2$/hexanes to 20% $CH_2Cl_2$/hexanes to give the title compound (1.5 g, 5.7 mmol) as a solid.

$^1$H NMR ($CDCl_3$, 300 MHz) d 7.55 (d, 2H), 7.43 (m, 2H), 7.32 (m, 1H), 7.12 (m, 1H), 7.07 (m, 1H), 6.87 (dd, 1H), 3.79 (s, 3H). FAB MS, $[M+H]^+$=262.

B. 3'-Methoxy-biphenyl-4-sulfonyl chloride.

3'-Methoxy-biphenyl-4-bromide (1.5 g, 5.7 mmol) is dissolved in 20 mL of THF and cooled to −78° C. To the solution is added a 2.5M solution of n-butyllithium in THF (2.3 mL, 5.7 mmol). The reaction mixture is stirred for 15 min and then is transferred via cannula to a solution of condensed sulfur dioxide gas (10 mL) in 40 mL of ether at −78° C. The solution is stirred for 30 minutes, allowed to warm to room temperature and then concentrated in vacuo. The resulting residue is triturated with ether to give 1.0 g of the lithium biarylsulfinate as a solid. The solid is suspended in 15 mL of hexanes and cooled to 0° C. To the suspension is added a 1M solution of sulfuryl chloride (4.2 mL, 4.2 mmol) in $CH_2Cl_2$. After 1 hour at 0° C., the resulting solution is concentrated. The residue is triturated with hexanes to give the title compound (0.60 g, 2.25 mmol) as a solid.

FAB MS, $[M+H]^+$=267.

C. 3'-Methoxy-biphenyl-4-sulfonic acid [1-3-(cyanobenzyl)-2-oxo-pyrrolidin-3-(S)-yl]-amide.

The title compound is prepared as described in EXAMPLE 1, Part D using 3'-methoxy-biphenyl-4-sulfonyl chloride in place of 2-naphthalene sulfonyl chloride.

$^1$H NMR ($CDCl_3$, 300 MHz) d 7.95 (d, 1H), 7.72 (m, 2H), 7.52 (m 1H), 7.40 (m, 5H), 7.16 (d, 1H), 7.10 (d, 1H), 6.95 (d, 1H), 5.33 (bs, 1H), 4.43 AB, 2H) 3.88 (s, 3H), 3.81 (m, 1H), 3.24 (m, 2H), 2.64 (m, 1H) 2.07 (m, 1H).

D. 3'-Methoxy-biphenyl-4-sulfonic acid {1-[3-(aminoiminomethyl)-benzyl]-2-oxo-pyrrolidin-3-(S)-yl}-amide trifluoroacetate.

The title compound is prepared as described in EXAMPLE 1, Part E using 3'-methoxy-biphenyl-4-sulfonic acid [1-[3-(cyanobenzyl)-2-oxo-pyrrolidin-3-(S)-yl]-amide as the starting material.

$^1$H NMR (DMSO-$d_6$, 300 MHz) d 9.30 (bs, 2H), 9.05 (bs, 2H), 8.20 (d, 1H), 7.90 (m, 4H), 7.71 (m, 2H), 7.55 (m, 2H), 7.40 (m, 2H), 7.28 (m, 2H), 6.99 (d, 1H), 4.43 (AB, 2H), 4.18 (m, 1H), 3.82 (s, 3H), 3.12 (m, 1H), 2.05 (m, 1H), 1.62 (m, 1H). FAB MS, $[M+H]^+$=479. Elemental analysis calculated with 1.0 mole of $H_2O$: C=53.11%, H=4.79%, N=9.18%, found C=53.31%, H=4.51%, N=9.15%.

EXAMPLE 6

Naphthalene-1-sulfonic acid {1-[3-(aminoiminomethyl)-benzyl]-2-oxo-pyrrolidin-3-(S)-yl}-amide trifluoroacetate.

A. Naphthalene-1-sulfonic acid [1-(3-cyanobenzyl)-2-oxo-pyrrolidin-3-(S)-yl]-amide.

The title compound is prepared as described in EXAMPLE 1, Part D using 1-naphthalene sulfonyl chloride in place of 2-naphthalene sulfonyl chloride.

$^1$H NMR ($CDCl_3$, 300 MHz) d 8.67 (d, 1H), 8.28 (d, 1H), 8.06 (d, 1H), 7.96 (d, 1H), 7.67 (m, 2H), 7.55 (m, 2H), 7.38 (m, 2H), 7.19 (s, 1H), 5.52 (bs, 1H), 4.37 (AB, 2H), 3.75 (m, 1H), 3.14 (m, 2H), 2.40 (m, 1H), 1.97 (m, 1H).

B. Naphthalene-1-sulfonic acid {1-[3-(aminoiminomethyl)-benzyl]-2-oxo-pyrrolidin-3-(S)-yl}-amide trifluoroacetate, The title compound is prepared as described in EXAMPLE 1, Part E using naphthalene-1-sulfonic acid [1-(3-cyanobenzyl)-2-oxo-pyrrolidin-3-(S)-yl]-amide as the starting material.

$^1$H NMR (DMSO-$d_6$, 300 MHz) d 9.30 (bs, 2H), 9.13 (bs, 2H), 8.65 (d, 1H), 8.51 (d, 1H), 8.32 (d, 1H), 8.22 (d, 1H), 8.09 (d, 1H), 7.64 (m, 5H), 7.50 (m, 3H), 4.40 (AB, 2H), 4.17 (m, 1H), 3.07 (m, 1H), 1.89 (m, 1H), 1.53 (m, 1H). FAB MS, [M+H]$^+$=423. Elemental analysis calculated with 1.0 mole of H$_2$O: C=51.98%, H=4.54%, N=10.10%, found C=52.20%, H=4.17%, N=9.73%.

EXAMPLE 7

5-Pyrid-2-yl-thiophene-2-sulfonic acid {1-[3-(aminoiminomethyl)-benzyl]-2-oxo-pyrrolidin-3-(S)-yl}-amide trifluoroacetate.

A. 5-Pyrid-2-yl-thiophene-2-sulfonic acid [1-(3-cyanobenzyl)-2-oxo-pyrrolidin-3-(S)-yl]-amide.

The title compound is prepared as described in

EXAMPLE 1, Part D using
5-pyrid-2-yl-thiophene-2-sulfonyl chloride in place
of 2-naphthalene sulfonyl chloride.

$^1$H NMR (CDCl$_3$, 300 MHz) d 8.62 (m, 1H), 7.78 (m, 1H), 7.69 (m, 1H), 7.58 (m, 2H), 7.50 (d, 1H), 7.46 (m, 2H), 7.20 (m, 2H), 5.43 (bs, 1H), 4.42 (AB, 2H), 3.98 (m, 1H), 3.26 (m, 2H), 2.68 (m, 1H), 2.15 (m, 1H).

B. 5-Pyrid-2-yl-thiophene-2-sulfonic acid {1-[3-(aminoiminomethyl)-benzyl]-2-oxo-pyrrolidin-3-(S)-yl}-amide trifluoroacetate.

The title compound is prepared as described in

EXAMPLE 1, Part E using
5-pyrid-2-yl-thiophene-2-sulfonic acid
[1-(3-cyanobenzyl)-2-oxo-pyrrolidin-3-(S)-yl]-amide
as the starting material.

$^1$H NMR (DMSO-d$_6$, 300 MHz) d 9.32 (bs, 2H), 9.13 (bs, 2H), 8.56 (d, 1H), 8.49 (d, 1H), 8.04 (d, 1H), 7.89 (m, 3H), 7.58 (m, 4H), 7.38 (m, 1H), 4.46 (AB, 2H), 4.23 (m, 1H), 3.16 (m, 2H), 2.16 (m, 1H), 1.70 (m, 1H). FAB MS, [M+H]$^+$=456. Elemental analysis calculated: C=43.93%, H=3.39%, N=10.24%, found C=44.04%, H=3.43%, N=10.26%.

EXAMPLE 8

Biphenyl-4-Sulfonic acid {1-[3-(aminoiminomethyl)-benzyl]-2-oxo-pyrrolidin-3-(S)-yl}-amide trifluoroacetate.

A. Biphenyl-4sulfonic acid [1-(3-cyanobenzyl)-2-oxo-pyrrolidin-3-(S)-yl]-amide

The title compound is prepared as described in

EXAMPLE 1, Part D using biphenyl-4-sulfonyl
chloride in place of 2-naphthalene sulfonyl
chloride.

$^1$H NMR (CDCl$_3$, 300 MHz) d 8.14 (s, 1H), 7.95 (d, 1H), 7.82 (d, 1H), 7.64 (m, 5H), 7.47 (m, 6H), 5.42 (bs, 1H), 4.42 (AB, 2H), 3.82 (m, 1H), 3.22 (m, 1H), 262 (m, 1H), 2.13 (m, 1H).

B. Biphenyl-4-8-sulfonic acid {1-[3-(aminoiminomethyl)-benzyl]-2-oxo-pyrrolidin-3-(S)-yl}-amide trifluoroacetate.

The title compound is prepared as described in

EXAMPLE 1, Part E using biphenyl-4-sulfonic
acid
[1-(3-cyanobenzyl)-2-oxo-pyrrolidin-3-(S)-yl]-amide
as the starting material.

$^1$H NMR (DMSO-d$_6$, 300 MHz) d 9.31 (bs, 2H), 9.14 (bs, 2H), 8.22 (d, 1H), 7.91 (m, 6H), 7.60 (m, 8H), 4.45 (AB, 2H), 4.16 (m, 1H), 3.12 (m, 1H), 2.07 (m, 1H), 1.65 (m, 1H). FAB MS, [M+H]$^+$=449. Elemental analysis calculated with 0.25 mole of H$_2$O: C=55.07%, H=4.53%, N=9.88%, found C=55.12%, H=4.41%, N=10.05%.

EXAMPLE 9

7-Methoxynaphthalene-2-sulfonic acid {1-[3-(aminoiminomethyl)-benzyl]-2-oxo-pyrrolidin-3-(S)-yl-}-amide trifluoroacetate.

A. 7-Methoxynaphthalene-2-sulfonyl chloride.

To a suspension of 7-hydroxynaphthalene-2-sulfonic acid, sodium salt (15.0 g, 60.9 mmol) in 150 mL of 2:1 H$_2$O/ethanol is added solid NaOH (2.68 g, 67.0 mmol) at room temperature. The mixture is stirred until a homogenous solution forms, and dimethyl sulfate (6.34 mL, 67.0 mmol) is then added. A precipitate eventually forms and the mixture is stirred over a period of 16 hours. The crude mixture is concentrated in vacuo and the residue is stirred in 100 mL of absolute EtOH as a slurry for 2 hours. The precipitate is filtered and dried. The solid is heated at reflux in 100 mL of 95% EtOH for 2 h, allowed to cool to room temperature, filtered and dried to give 12.6 g of crude 7-methoxynaphthalene-2-sulfonic acid, sodium salt. A mixture of the sulfonic acid, sodium salt (12.6 g, 48.6 mmol) in 20 mL of phosphorous oxychloride and phosphorous pentachloride (13.2 g, 63.2 mmol) is heated slowly to 60° C. until a homogenous solution forms and then is heated at 120° C. for 4 hours. The resulting mixture is cooled in an ice bath and a mixture of ice/ice water is added slowly with stirring. The mixture is diluted with water and extracted with CHCl$_3$ (2×100 mL). The combined organic layers are washed successively with water, saturated NaHCO$_3$ solution and saturated NaCl. The organic phase is dried over anhydrous MgSO$_4$, filtered and concentrated to give 10.0 g of a crude oil. The crude product is purified by column chromatography in a gradient of 5% EtOAc/hexanes to 30% EtOAc/hexanes to afford the title compound (3.80 g, 14.8 mmol) as a white crystalline solid.

$^1$H NMR (CDCl$_3$, 300 MHz) d 8.49 (d, 1H), 7.96 (d, 1H), 7.85 (d, 2H), 7.39 (dd, 1H), 7.29 (d, 1H), 3.99 (s, 3H). EI MS, [M]$^+$=256.

The 8-chloro-7-methoxynaphthalene-2-sulfonyl chloride (1.49 g, 5.12 mmol) is also isolated as a minor by-product from the above procedure.

$^1$H NMR (CDCl$_3$, 300 MHz) d 8.95 (d, 1H), 8.01 (d, 1H), 7.90 (d, 2H), 7.55 (d, 1H), 4.09 (s, 3H). EI MS, [M]$^+$=290.

B. 7-Methoxynaphthalene-2-sulfonic acid [1-(3-cyanobenzyl)-2-oxo-pyrrolidin-3-(S)-yl]-amide.

The title compound is prepared from 3-(3-(S)-amino-2-oxo-pyrrolidin-1-ylmethyl)-benzonitrile hydrochloride as in EXAMPLE 1, Part D using 7-methoxynaphthalene-2-sulfonyl chloride. The crude product is triturated from 50% EtOAc/hexanes solution to give the title compound as a beige solid.

$^1$H NMR (CDCl$_3$, 300 MHz) d 8.38 (d, 1H), 7.91 (d, 1H), 7.81 (d, 1H), 7.73 (dd, 1H), 7.59 (m, 1H), 7.42 (m, 3H), 7.30 (dd, 1H), 7.25 (m, 1H), 5.39 (d, 1H), 4.45 (AB, 2H), 3.92 (s, 3H), 3.75 (m, 1H), 3.20 (m, 2H), 2.60 (m, 1H), 2.10 (m, 1H).

C. 7-Methoxynaphthalene-2-sulfonic acid {1-[3-(aminoiminomethyl)-benzyl]-2-oxo-pyrrolidin-3-(S)-yl}-amide trifluoroacetate.

7-Methoxynaphthalene-2-sulfonic acid [1-(3-cyanobenzyl)-2-oxo-pyrrolidin-3-(S)-yl]-amide is dissolved in 10 mL of a 2:1 mixture of EtOH/CH$_2$Cl$_2$ and converted to the title compound as in EXAMPLE 1, Part E. The imidate intermediate is formed over a period of 18 hours at room temperature. The amidine formation occurred over a period of 18 hours at room temperature. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) d 9.41 (bs, 2H), 9.29 (bs, 2H), 8.33 (d, 1H), 8.19 (d, 1H), 7.96 (d, 1H), 7.87 (d, 1H), 7.68 (dd, 1H), 7.64 (m, 1H), 7.50 (m, 4H), 7.27 (dd, 1H), 4.36 (AB, 2H), 4.16 (dd, 1H), 3.48 (s, 3H), 3.04 (m, 2H), 1.93 (m, 1H), 1.59 (m, 1H). FAB MS, [M+H]$^+$=453. Elemental analysis calculated with 1.7 mole of $H_2O$: C=50.28%, H=4.79%, N=9.38%; found C=50.27%, H=4.14%, N=9.07%.

7-Methoxynaphthalene-2-sulfonic acid {1-[3-(aminoiminomethyl)-benzyl]-2-oxo-pyrrolidin-(3R)-yl}-amide trifluoroacetate is prepared from 7-methoxynaphthalene-2-sulfonic acid [1-(3-cyanobenzyl)-2-oxo-pyrrolidin-(3R)-yl]-amide as above.

EXAMPLE 10

7-Ethoxynaphthalene-2-sulfonic acid {1-[3-(aminoiminomethyl)-benzyl]-2-oxo-pyrrolidin-3-(S)-yl}-amide trifluoroacetate, A. 7-Ethoxynaphthalene-2-sulfonyl chloride.

A 60% dispersion of sodium hydride (0.74 g, 18.45 mmol) in mineral oil is washed with hexanes twice and suspended in 35 mL of DMF. To this mixture is added slowly via an addition funnel 7-hydroxynaphthalene-2-sulfonic acid, sodium salt (2.50 g, 10.1 mmol) in 50 mL of DMF at room temperature. The reaction mixture is stirred for 75 min during which time mild bubbling is observed ($H_2$ evolution). The mixture is treated with bromoethane (2.42 mL, 32.5 mmol) and stirred for 16 hours at room temperature. A little ice is added to decompose the excess NaH and the resultant mixture is concentrated in vacuo. The residue is suspended in acetone and concentrated in vacuo two times and then is dried under high vacuum. The solid is suspended in acetone, filtered and dried to yield the crude 7-ethoxynaphthalene-2-sulfonic acid, sodium salt as a beige solid. A mixture of the sulfonic acid, sodium salt (3.77 g) in 10 mL of thionyl chloride is heated at 80° C. for 2 hours. The mixture is allowed to cool to room temperature and concentrated in vacuo. The residue is diluted in EtOAc and washed successively with water (2×), saturated $NaHCO_3$ solution and saturated NaCl. The organic layer is dried over anhydrous $MgSO_4$, filtered and concentrated to yield 2.65 g of a crude brown oil. The crude product is purified by column chromatography in a gradient of 10% EtOAc/hexanes to 20% EtOAc/hexanes to afford the title compound (1.67 g, 6.17 mmol) as a pale yellow solid.

$^1$H NMR (CDCl$_3$, 300 MHz) d 8.46 (s, 1H), 7.97 (d, 1H), 7.85 (d, 1H), 7.84 (d, 1H), 7.38 (dd, 1H), 7.28 (s, 1H), 4.19 (q, 2H), 1.50 (t, 3H).

B. 7-Ethoxynaphthalene-2-sulfonic acid [1-(3-cyanobenzyl)-2-oxo-pyrrolidin-3-(S)-yl]-amide.

The title compound is prepared from 3-(3-(S)-amino-2-oxo-pyrrolidin-1-ylmethyl)-benzonitrile hydrochloride as in EXAMPLE 1, Part D using 7-ethoxynaphthalene-2-sulfonyl chloride. The crude product is triturated from 50% EtOAc/hexanes solution to give the title compound as a beige solid.

$^1$H NMR (CDCl$_3$+DMSO-$d_6$, 300 MHz) d 8.27 (d, 1H), 7.80 (d, 1H), 7.67 (m, 2H), 7.47 (m, 1H), 7.41 (bs, 1H), 7.34 (d, 2H), 7.17 (m, 3H), 4.34 (AB, 2H), 4.06 (q, 2H), 3.87 (m, 1H), 3.04 (m, 2H), 2.25 (m, 1H), 1.81 (m, 1H), 1.39 (t, 3H).

C. 7-Ethoxynaphthalene-2-sulfonic acid {1-[3-(aminoiminomethyl)-benzyl]-2-oxo-pyrrolidin-3-(S)-yl}-amide trifluoroacetate.

7-Ethoxynaphthalene-2-sulfonic acid [1-(3-cyanobenzyl)-2-oxo-pyrrolidin-3-(S)-yl]-amide is dissolved in 10 mL of a 2:1 mixture of EtOH/$CH_2Cl_2$ and converted to the title compound as in EXAMPLE 1, Part E. The imidate intermediate is formed over a period of 18 hours at room temperature. The amidine formation occurred over a period of 48 hours at room temperature. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) d 9.41 (bs, 2H), 9.33 (bs, 2H), 8.37 (d, 1H), 8.24 (d, 1H), 8.02 (d, 1H), 7.94 (d, 1H), 7.73 (dd, 1H), 7.70 (d, 1H), 7.56 (m, 4H), 7.32 (dd, 1H), 4.43 (AB, 2H), 4.17 (q, 2H), 4.15 (m, 1H), 3.10 (m, 2H), 2.00 (m, 1H), 1.59 (m, 1H), 1.40 (t, 3H). FAB MS, [M+H]$^+$=467. Elemental analysis calculated with 1.9 mole of $H_2O$: C=50.91%, H=5.04%, N=9.13%; found C=50.92%, H=4.44%, N=8.57%.

EXAMPLE 11

5-Chloro-6-methoxynaphthalene-2-sulfonic acid {1-[3-(aminoiminomethyl)-benzyl]-2-oxo-pyrrolidin-3-(S)-yl}-amide trifluoroacetate.

A. 5-Chloro-6-methoxynaphthalene-2-sulfonyl chloride.

The title compound is prepared from 6-hydroxynaphthalene-2-sulfonic acid, sodium salt as in EXAMPLE 9, Part A. The crude product mixture is purified by column chromatography in a gradient of 5% EtOAc/hexanes to 10% EtOAc/hexanes to provide the title compound as a minor by-product.

$^1$H NMR (CDCl$_3$, 300 MHz) d 8.57 (d, 1H), 8.42 (d, 1H), 8.05 (dd, 1H), 8.00 (d, 1H), 7.50 (d, 1H), 4.10 (s, 3H).

B. 5-chloro-6-methoxynaphthalene-2-sulfonic acid [1-(3-Cyanobenzyl)-2-oxo-pyrrolidin-3-(S)-yl]-amide.

The title compound is prepared from 3-(3-(S)-amino-2-oxo-pyrrolidin-1-ylmethyl)-benzonitrile hydrochloride as in EXAMPLE 1, Part D using 5-chloro- 6-methoxynaphthalene-2-sulfonyl chloride. The crude product is triturated from EtOAc to give the title compound as a beige solid.

$^1$H NMR (CDCl$_3$, 300 MHz) d 8.44 (d, 1H), 8.38 (d, 1H), 7.98 (dd, 1H), 7.91 (d, 1H), 7.60 (m, 1H), 7.42 (m, 4H), 5,51.(d, 1H), 4.45 (AB, 2H), 4,09.(s, 3H), 3.80 (m, 1H), 3.20 (m, 2H), 2.60 (m, 1H), 2.10 (m, 1H).

C. 5-Chloro-6-methoxynaphthalene-2-sulfonic acid {1-[3-(aminoiminomethyl)-benzyl]-2-oxo-pyrrolidin-3-(S)-yl}-amide trifluoroacetate.

5-Chloro-6-methoxynaphthalene-2-sulfonic acid [1-(3-cyanobenzyl)-2-oxo-pyrrolidin-3-(S)-yl]-amide is dissolved in 10 mL of a 2:1 mixture of EtOH/$CH_2Cl_2$ and converted to the title compound as in EXAMPLE 1, Part E. The imidate intermediate is formed over a period of 16 hours at room temperature. The amidine formation occurred over a period of 24 hours at room temperature. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) d 9.29 (bs, 2H), 9.10 (bs, 2H), 8.52 (d, 1H), 8.29 (d, 1H), 8.23 (d, 1H), 8.21 (d, 1H), 7.98 (dd, 1H), 7.71 (d, 1H), 7.67 (d, 1H), 7.58 (d, 1H), 7.54 (bs, 1H), 7.52 (d, 1H), 4.41 (AB, 2H), 4.16 (m, 1H), 4.04 (s, 3H), 3.09 (m, 2H), 2.01 (m, 1H), 1.59 (m, 1H). FAB MS, [M+H]$^+$=487. Elemental analysis calculated with 1.5 mole of $H_2O$: C=47.88%, H=4.32%, N=8.93%; found C=47.88%, H=3.88%, N=8.48%.

EXAMPLE 12

5-Chloro-6,7-dimethoxynaphthalene-2-sulfonic acid {1-[3-(aminoiminomethyl)benzyl-]-2-oxo-pyrrolidin-3-(S)-yl}-amide trifluoroacetate.

A. 5-Chloro-6,7-dimethoxynaphthalene-2-sulfonyl chloride.

The title compound is prepared from 6,7-dihydroxynaphthalene-2-sulfonic acid, sodium salt hemihydrate as in EXAMPLE 9, Part A. The crude product mixture is purified by column chromatography in a gradient of 5% EtOAc/hexanes to 30% EtOAc/hexanes to give the title compound as a minor by-product.

$^1$H NMR (CDCl$_3$, 300 MHz) d 8.48 (d, 1H), 8.38 (d, 1H), 7.45 (dd, 1H), 7.30 (s, 1H), 4.05 (s, 3H), 4.00 (s, 3H).

B. 5-Chloro-6,7-dimethoxynaphthalene-2-sulfonic acid [1-(3-cyanobenzyl)-2-oxo-pyrrolidin-3-(S)-yl]-amide.

The title compound is prepared from 3-(3-(S)-amino-2-oxo-pyrrolidin-1-ylmethyl)-benzonitrile hydrochloride as in EXAMPLE 1, Part D using 5-chloro-6,7-dimethoxynaphthalene-2-sulfonyl chloride. The crude product is triturated from EtOAc to give the title compound as a beige solid.

$^1$H NMR (CDCl$_3$, 300 MHz) d 8.49 (d, 1H), 8.25 (d, 1H), 7.86 (dd, 1H), 7.55 (m, 1H), 7.40 (m, 3H), 7.20 (s, 1H), 5.89 (m, 1H), 4.44 (AB, 2H), 4.03 (s, 3H), 4.00 (s, 3H), 3.86 (m, 1H), 3.20 (m, 2H), 2.59 (m, 1H), 2.07 (m, 1H).

C. 5-Chloro-6,7-dimethoxynaphthalene-2-sulfonic acid {1-[3-aminoiminomethyl)-benzyl]-2-oxo-pyrrolidin-3-(S)-yl}-amide trifluoroacetate.

5-Chloro-6,7-dimethoxynaphthalene-2-sulfonic acid [1-(3-cyanobenzyl)-2-oxo-pyrrolidin-3-(S)-yl]-amide is dissolved in 10 mL of a 2:1 mixture of EtOH/CH$_2$Cl$_2$ and converted to the title compound as in EXAMPLE 1, Part E. The imidate intermediate is formed over a period of 24 hours at room temperature. The amidine formation occurred over a period of 24 hours at room temperature. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) d 9.29 (bs, 2H), 9.12 (bs, 2H), 8.43 (d, 1H), 8.30 (d, 1H), 8.19 (d, 1H), 7.87 (dd, 1H), 7.73 (s, 1H), 7.67 (m, 1H), 7.55 (m, 3H), 4.41 (AB, 2H), 4.14 (m, 1H), 3.97 (s, 3H), 3.89 (s, 3H), 3.08 (m, 2H), 1.99 (m, 1 H), 1.60 (m, 1H). ISP MS, [M+H]$^+$=517. Elemental analysis calculated with 1.5 mole of H$_2$O: C=47.38%, H=3.91%, N=8.14%; found C=47.40%, H=4.05%, N=8.22%.

EXAMPLE 13

Dibenzofuran-2-sulfonic acid {1-[3-(aminoiminomethyl)-benzyl]-2-oxo-pyrrolidin-3-(S)-yl}-amide trifluoroacetate.

A. Dibenzofuran-2-sulfonic acid [1-(3-cyanobenzyl)-2-oxo-pyrrolidin-3-(S)-yl]-amide.

The title compound is prepared from 3-(3-(S)-amino-2-oxo-pyrrolidin-1-ylmethyl)-benzonitrile hydrochloride as in EXAMPLE 1, Part D using 2-dibenzofuransulfonyl chloride. The crude product is triturated from EtOAc to give the title compound as a beige solid.

$^1$H NMR (CDCl$_3$, 300 MHz) d 8.59 (d, 1H), 8.04 (dd, 1H), 7.95 (d, 1H), 7.64 (d, 1H), 7.60 (m, 1H), 7.52 (m, 2H), 7.40 (m, 5H), 4.42 (AB, 2H), 3.89 (m, 1H), 3.19 (m, 2H), 2.57 (m, 1H), 2.08 (m, 1H).

B. Dibenzofuran-2-sulfonic acid {1-[3-(aminoiminomethyl)-benzyl]-2-oxo-pyrrolidin-3-(S)-yl}-amide trifluoroacetate.

Dibenzofuran-2-sulfonic acid [1-(3-cyanobenzyl)-2-oxo-pyrrolidin-3-(S)-yl]-amide is dissolved in 10 mL of a 2:1 mixture of EtOH/CH$_2$Cl$_2$ and converted to the title compound as in EXAMPLE 1, Part E. The imidate intermediate is formed over a period of 24 hours at room temperature. The amidine formation occurred over a period of 40 hours at room temperature. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) d 9.30 (bs, 2H), 9.12 (bs, 2H), 8.72 (d, 1H), 8.30 (d, 1H), 8.22 (d, 1H), 8.04 (dd, 1H), 7.92 (d, 1H), 7.79 (d, 1H), 7.67 (m, 1H), 7.61 (m, 2H), 7.56 (m, 1H), 7.55 (bs, 1H), 7.48 (m, 1H), 4.42 (AB, 2H), 4.19 (m, 1H), 3.10 (m, 2H), 2.04 (m, 1H), 1.61 (m, 1H). FAB MS, [M+H]$^+$=463. Elemental analysis calculated with 1.3 mole of H$_2$O: C=51.97%, H=4.31%, N=9.32%; found C=51.99%, H=3.76%, N=9.00%.

EXAMPLE 14

7-Aminonaphthalene-2-sulfonic acid {1-[3-(aminoiminomethyl)-benzyl]-2-oxo-pyrrolidin-3-(S)-yl}-amide ditrifluoroacetate.

A. N-Cbz-7-aminonaphthalene-2-sulfonyl chloride.

To a suspension of 7-aminonaphthalene-2-sulfonic acid, sodium salt (3.0 g, 12.2 mmol) in 70 mL of water is added solid NaOH (0.98 g, 24.0 mmol) at room temperature. The mixture is stirred for 30 minutes, and benzyl chloroformate (3.43 mL, 24.0 mmol) is then added. The resulting mixture is stirred over a period of 16 hours. The crude product is treated as in EXAMPLE 9, Part A, to give 4.18 g of crude N-CBz-7-aminonaphthalene-2-sulfonic acid, sodium salt. A mixture of the sulfonic acid, sodium salt (4.18 g, 11.0 mmol) in 12 mL of thionyl chloride is heated at 80° C. for 3 hours. The mixture is allowed to cool to room temperature and concentrated in vacuo. The residue is diluted with EtOAc and washed successively with water (2x), saturated NaHCO$_3$ solution and saturated NaCl. The organic layer is dried over anhydrous MgSO$_4$, filtered and concentrated to give a brown oil. The crude product is purified by column chromatography in a gradient of 10% EtOAc/hexanes to 30% EtOAc/hexanes to afford the title compound (1.76 g, 4.68. mmol) as a beige solid.

$^1$H NMR (CDCl$_3$, 300 MHz) d 8.38 (s, 1H), 8.12 (s, 1H), 7.88 (d, 1H), 7.80 (d, 2H), 7.60 (dd, 1H), 7.34 (m, 5H), 7.27 (s, 1H), 5.21 (s, 2H).

B. N-Cbz-7-aminonaphthalene-2-sulfonic acid [1-(3-cyanobenzyl)-2-oxo-pyrrolidin-3-(S)-yl]-amide.

The title compound is prepared from 3-(3-(S)-amino-2-oxo-pyrrolidin-1-ylmethyl;)-benzonitrile hydrochloride as in EXAMPLE 1, Part D using N-Cbz-7-aminonaphthalene-2-sulfonyl chloride in place of 7-methoxynaphthalene-2-sulfonyl chloride. The crude product is purified by column chromatography using a gradient of 10% EtOAc/CH$_2$CL$_2$ to 25% EtOAc/CH$_2$CL$_2$ to give the title compound as a solid.

$^1$H NMR (CDCl$_3$, 300 MHz) d 8.31 (s, 1H), 8.03 (s, 1H), 7.71 (m, 3H), 7.55 (m, 2H), 7.40 (m, 9H), 5.78 (s, 1H), 5.25 (d, 1H), 5.21 (d, 1H), 4.41 (AB, 2H), 3.85 (m, 1H), 3.15 (m, 2H), 2.53 (m, 1H), 2.02 (m, 1H).

C. 7-Aminonaphthalene-2-sulfonic acid {1-[3-(aminoiminomethyl)-benzyl]-2-oxo-pyrrolidin-3-(S)-yl}-amide ditrifluoroacetate.

N-Cbz-7-aminonaphthalene-2-sulfonic acid [1-(3-cyanobenzyl)-2-oxo-pyrrolidin-3-(S)-yl]-amide is dissolved in 10 mL of a 2:1 mixture of EtOH/CH$_2$Cl$_2$ and converted to the title compound as in EXAMPLE 1, Part E. The imidate intermediate is formed over a period of 18 hours at room temperature. The amidine formation occurred over a period of 18 hours at room temperature. The crude product is purified by RP-HPLC eluting in a gradient of 10% CH$_3$CN/ H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) d 9.29 (bs, 2H), 9.20 (bs, 2H), 8.11 (d, 1H), 8.08 (s, 1H), 7.82 (d, 1H), 7.72 (d, 1H), 7.67 (m, 1H), 7.55 (m, 3H), 7.48 (dd, 1H), 7.13(dd, 1H), 7.00(d, 1H),5.11 (bs, 3H),4.42(AB, 2H), 4.12(m, 1H),3.06 (m, 2H), 1.94 (m, 1H), 1.56 (m, 1H). FAB MS, [M+H]$^+$= 438. Elemental analysis calculated with 0.8 mole of H$_2$O: C=45.96%, H=3.94%, N=10.31%; found C=45.97%, H=4.02%, N=10.41%.

EXAMPLE 15

Naphthalene-2-sulfonic acid {1-[4-(aminoiminomethyl)- benzyl]-2-oxo-pyrrolidin-3-(S)-yl}-amide trifluoroacetate.

A. [1-(4-Cyanobenzyl)-2-oxo-pyrrolidin-3-(S)-yl]-car- bamic acid tert-butyl ester.

The title compound is prepared from Boc-L-Asp(H)-OBn as in EXAMPLE 1, Part B, using p-cyanobenzylamine hydrochloride in place of m-cyanobenzylamine hydrochlo- ride. The crude residue is purified by column chromatogra- phy eluting with a gradient of 20% EtOAc/CH$_2$Cl$_2$ to 40% EtOAc/CH$_2$Cl$_2$ to give the title compound as a white solid.

$^1$H NMR (CDCl$_3$, 300 MHz) d 7.62 (d, 2H), 7.31 (d, 2H), 5.15 (bs, 1H), 4.53 (AB, 2H), 4.21 (m, 1H), 3.24 (m, 2H), 2.61 (m, 1H), 1.90 (m, 1H), 1.46 (s, 9H).

B. 4-(3-(S)-Amino-2-oxo-pyrrolidin-1-ylmethyl)-ben- zonitrile hydrochloride.

The title compound is prepared as a white solid from [1-(4-cyanobenzyl)-2-oxo-pyrrolidin-3-(S)-yl]-carbamic acid tert-butyl ester as described in EXAMPLE 1, Part C.

$^1$H NMR (DMSO-d$_6$, 300 MHz) d 8.65 (bs, 3H), 7.81 (d, 2H), 7.49 (d, 2H), 4.54 (AB, 2H), 4.08 (m, 1H), 3.30 (m, 2H), 2.40 (m, 1H), 2.01 (m, 1H).

C. Naphthalene-2-sulfonic acid [1-(4-cyanobenzyl)-2- oxo-pyrrolidin-3-(S)-yl]-amide.

The title compound is prepared from 4-(3-(S)-amino-2- oxo-pyrrolidin-1-ylmethyl)-benzonitrile hydrochloride as in EXAMPLE 1, Part D. The crude product is triturated from EtOAc to give the title compound as a white solid. $^1$H NMR (DMSO-d$_6$, 300 MHz) d 8.50 (s, 1H), 8.00 (m, 2H), 7.93 (m, 3H), 7.65 (m, 5H), 7.28 (m, 1H), 4.45 (AB, 2H), 3.80 (m, 1H), 3.20 (m, 2H), 2.55 (m, 1H), 2.11 (m, 1H).

D. Naphthalene-2-sulfonic acid {1-[4-(aminoiminom- ethyl)-benzyl]-2-oxo-pyrrolidin-3-(S)-yl}-amide trifluoro- acetate.

Naphthalene-2-sulfonic acid [1-(4-cyanobenzyl)-2-oxo- pyrrolidin-3-(S)-yl]-amide is dissolved in 10 mL of a 2:1 mixture of EtOH/CH$_2$Cl$_2$ and converted to the title com- pound as in EXAMPLE 1, Part E. The imidate intermediate is formed over a period of 18 hours at room temperature. The amidine formation occurred over a period of 48 hours at room temperature. The crude product is purified by RP- HPLC eluting in a gradient of 10% CH$_3$CN/H$_2$O (0.1% TFA) to 60% CH$_3$CN/H$_2$O (0.1% TFA) and the appropriate product fractions are lyophilized to provide the title com- pound as a white solid.

$^1$H NMR (DMSO-d$_6$, 300 MHz) d 9.26 (bs, 2H), 9.10 (bs, 2H), 8.49 (d, 1H), 8.30(d, 1H), 8.12 (d, 1H),8.11 (d, 1H), 8.03(d, 1H), 7.88(dd, 1H), 7.74(d, 2H), 7.68 (m, 2H), 7.40 (d, 2H), 4.44 (AB, 2H), 4.17 (m, 1H), 3.07 (m, 2H), 2.01 (m, 1H), 1.58 (m, 1H). FAB MS, [M+H]$^+$=423. Elemental analysis calculated with 1.4 mole of H$_2$O: C=51.32%, H=4.63%, N=9.97%, found C=51.32%, H=4.36%, N=9.78%.

EXAMPLE 16

7-Methoxynaphthalene-2-sulfonic acid [1-(3-aminomethyl- benzyl)-2-oxo-pyrrolidin-3-(S)-yl]-amide trifluoroacetate.

To a solution of 7-methoxynaphthalene-2-sulfonic acid [1-(3-cyanobenzyl)-2-oxo-pyrrolidin-3-(S)-yl]-amide (0.12 g, 0.27 mmol) in 10 mL of 7.0N NH3/MeOH is added a catalytic amount of 5% rhodium on alumina powder. The resulting mixture is hydrogenated at room temperature on a Paar apparatus at 50 p.s.i. for 3 hours. The crude mixture is filtered through a pad of Celite, washed with MeOH (2×10 mL) and concentrated in vacuo. The crude product is puri- fied by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) d 8.39 (d, 1H), 8.21 (d, 1H), 8.13 (bs, 3H), 8.01 (d, 1H), 7.93 (d, 1H), 7.71 (dd, 1H), 7.55 (d, 1H), 7.32 (m, 3H), 7.20 (m, 2H), 4.30 (AB, 2H), 4.10 (m, 1H), 4.00 (m, 2H), 3.90 (s, 3H), 3.03 (m, 2H), 1.96 (m, 1H), 1.55 (m, 1H). FAB MS, [M+H]$^+$=440.

EXAMPLE 17

Naphthalene-2-sulfonic acid {1-[3-(aminoiminomethyl)- benzyl]-2-oxo-pyrrolidin-3-(S)-yl}methyl amide trifluoro- acetate.

A. Naphththalene-2-sulfonic acid [1-(3-cyanobenzyl)-2- oxo-pyrrolidin-3-(S)-yl]methyl amide.

Naphthalene-2-sulfonic acid [1-(3-cyanobenzyl)-2-oxo- pyrrolidin-3-(S)-yl]amide (0.30 g, 0.74 mmol) is dissolved in 9 mL of an 8:1 mixture of THF/DMF and cooled to 0° C. Sodium hydride (30 mg of a 60% dispersion in mineral oil, 0.75 mmol) is added and the solution is stirred for 15 minutes. To the mixture is added methyl iodide (0.33 g, 2.34 mmol). The cooling bath is removed and the solution is stirred at room temperature for 2 hours. The solution is poured into a separatory funnel and diluted with 100 mL of EtOAc. The organic layer is washed with 1N HCl, dried over MgSO$_4$ and concentrated. The residue is purified by column chromatography eluting with 10% EtOAc/CH$_2$Cl$_2$ to give the title compound (0.23 g, 0.52 mmol) as a solid.

$^1$H NMR (CDCl$_3$, 300 MHz) d 8.52 (s, 1H), 8.00 (m, 4H), 7.62 (m, 4H), 7.48 (m, 3H), 4.95 (m, 1H), 4.45 (AB, 2H), 3.20 (m, 1H),.2.80 (s, 3H), 2.37 (m, 1H), 2.05 (m, 1H). FAB MS, [M+H]$^+$=420.

B. Naphthalene-2-sulfonic acid {1-[3-(aminoiminom- ethyl)-benzyl]-2-oxo-pyrrolidin-3-(S)-yl}methyl amide trif- luoroacetate.

The title compound is prepared as described in EXAMPLE 1, Part E using naphthalene-2-sulfonic acid [1-(3-cyanobenzyl)-2-oxo-pyrrolidin-3-(S)yl]methyl amide as the starting material.

$^1$H NMR (DMSO-d$_6$, 300 MHz) d 9.30 (bs, 2H), 9.10 (bs, 2H), 8.52 (s, 1H), 8.15 (m, 3H), 7.85 (d, 1H), 7.68 (m, 3H), 7.55 (m, 3H), 4.98 (m, 1H), 4.42 (AB, 2H), 3.15 (m, 2H), 2.69 (s, 3H), 2.02 (m, 1H), 1.82 (m, 1H). FAB MS, [M+H]$^+$=437. Elemental analysis calculated with 2.0 mole of H$_2$O: C=51.19%, H=4.985%, N=9.55%, found C=51.01%, H=4.35%, N—9.10%.

EXAMPLE 18

Naphthalene-2-sulfonic acid {1-[3-(aminoiminomethyl)- benzyl]-pyrrolidin-3-(S)-yl}-amide ditrifluoroacetate.

A. Naphthalene-2-sulfonic acid-N-Boc-3-(S)-aminopyr- rolidine.

N-Boc-3-aminopyrrolidine (1.09 g, 5.83 mmol) is dis- solved in 30 mL of CH$_2$Cl$_2$. To the solution is added triethylamine (0.61 g, 6.02 mmol) followed by 2-naphtha- lene sulfonyl chloride (1.32 g, 5.83 mmol). The reaction mixture is stirred for 4 hours. The crude mixture is diluted with 150 mL of EtOAc and washed with 1N HCl, 10% $Na_2CO_3$ and saturated NaCl. The organic layer is dried over $MgSO_4$, filtered and concentrated to give the title compound (2.19 g, 5.8 mmol) as an oil.

$^1$H NMR (CDCl$_3$, 300 MHz) d 8.42 (s, 1H), 7.95 (m, 4H), 7.66 (m, 3H), 5.03 (bs, 1H), 3.88 (m, 1H), 3.30 (m, 2H), 3.10 (m, 1H), 1.95 (m, 2H), 1.45 (s, 9H).

B. Naphthalene-2-sulfonic acid-pyrrolidin-3-(S)-yl-amide trifluoroacetate.

Naphthalene-2-sulfonic acid-N-Boc-3-(S)-aminopyrrolidine (1.8 g, 4.78 mmol) is dissolved in 50 mL of $CH_2Cl_2$. Trifluoroacetic acid (8 mL) is added dropwise. The reaction mixture is stirred for 16 hours. The solution is concentrated in vacuo and then reconcentrated from toluene to give the title compound (1.8 g, 4.64 mmol).

$^1$H NMR (CDCl$_3$, 300 MHz) d 9.10 (bs, 1H), 8.82 (bs, 1H), 8.39 (s, 1H), 7.90 (m, 3H), 7.78 (d, 1H), 7.61 (m, 3H), 4.00 (bs, 1H), 3.51 (m, 2H), 3.38 (m, 2H), 2.05 (m, 2H).

C. Naphthalene-2-sulfonic acid [1-(3-cyanobenzyl)-pyrrolidin-3-(S)-yl]-amide.

Naphthalene-2-sulfonic acid-pyrrolidin-3-(S)-yl-amide trifluoroacetate (0.52 g, 1.34 mmol) is dissolved in 7 mL of DMF. Triethylamine (0.16 g, 1.6 mmol) is added and the reaction mixture is cooled to 0° C. a-Bromo-m-tolunitrile (0.25 g, 1.27 mmol) is added and the mixture is warmed to room temperature and stirred for 2 hours. The reaction mixture is diluted with 150 mL of EtOAc and the solution is washed with 1N HCl, 10% $Na_2CO_3$ and saturated NaCl. The organic layer is dried over $MgSO_4$, filtered and concentrated. The residue is purified by column chromatography eluting with 50% EtOAc/$CH_2Cl_2$ to give the title compound (0.20 g, 0.51 mmol) as an oil.

$^1$H NMR (CDCl$_3$, 300 MHz) d 8.40 (s, 1H), 7.95 (m, 3H), 7.80 (d, 1H), 7.64 (m, 2H), 7.50 (m, 3H), 7.31 (m, 1H), 5.04 (d, 1H), 3.92 (m, 1H), 3.05 (q, 2H), 2.70 (m, 1H), 2.40 (m, 2H), 2.18 (m, 2H), 1.59 (m, 1H).

D. Naphthalene-2-sulfonic acid {1-[3-(aminoiminomethyl)-benzyl]-pyrrolidin-3-(S)-yl}-amide ditrifluoroactetate.

The title compound is prepared as in EXAMPLE 1, Part E using naphthalene-2-sulfonic acid [1-(3-cyanobenzyl)-pyrrolidin-3-(S)-yl]-amide as the starting material.

$^1$H NMR (CDCl$_3$, 300 MHz) d 10.6 (bs, 1H), 9.32 (bs, 3H), 8.45 (s, 1H), 8.14 (m, 2H), 8.05 (d, 1H), 7.72 (m, 9H), 3.85 (m, 1H), 3.65 (AB, 2H), 3.25 (m, 4H), 1.95 (m, 2H). FAB MS, [M+H]$^+$=409. Elemental analysis calculated with 1.25 mole of H$_2$O: C=47.39%, H=4.36%, N=8.50%, found C=47.12%, H=3.97%, N=8.50%.

EXAMPLE 19

7-Methoxynaphthalene-2-sulfonic acid {1-[3-(aminoiminomethyl)-benzyl]-2.5-dioxo-pyrrolidin-3-(S)-yl}-amide trifluoroacetate.

A. N-Boc-Asp-(m-cyanobenzylamine)-OBn.

Boc-Asp-OBn (3.23 g, 10 mmol) is dissolved in 100 mL of THF. Triethylamine (2.53 g, 25 mmol) is added followed by m-cyanobenzylamine hydrochloride (1.75 g, 10.4 mmol). The reaction mixture is cooled to −10° C., and the BOP reagent (4.42 g, 10 mmol) is added. The mixture is stirred for 16 hours. The crude mixture is diluted with 200 mL of EtOAc and washed with 1N HCl, 10% $Na_2CO_3$ and saturated NaCl. The organic layer is dried over $MgSO_4$, filtered and concentrated. The residue is purified by column chromatography eluting with 20% EtOAc/$CH_2Cl_2$ to give the title compound (3.4 g, 7.8 mmol) as a solid.

$^1$H NMR (CDCl$_3$, 300 MHz) d 7.48 (m, 9H), 7.00 (bs, 1H), 5.68 (bs, 1H), 5.15 (AB, 2H), 4.60 (m, 2H), 4.35 (dd, 1H), 3.12 (dd, 1H), 2.75 (dd, 1H), 1.45 (s, 9H).

B. [1-(3-Cyanobenzyl)-2,5-dioxo-pyrrolidin-3-(S)-yl]-carbamic acid tert-butyl ester.

N-Boc-Asp-(m-cyanobenzylamine)-OBn (1.0 g, 2.08 mmol) is dissolved in 20 mL of THF and cooled to −78° C. A 1M solution of lithium hexamethyldisilylazide (4.8 mL, 4.8 mmol) in THF is added dropwise. The mixture is Stirred for 20 min and 20 mL of saturated NH4Cl is added. The solution is extracted with EtOAc and then washed with 1N HCl, 10% $Na_2CO_3$ and saturated NaCl. The organic layer is dried over $MgSO_4$, filtered and concentrated. The residue is purified by column chromatography eluting with 20% EtOAc/$CH_2Cl_2$ to give the title compound (0.65 g, 1.8 mmol) as a solid.

$^1$H NMR (CDCl$_3$, 300 MHz) d 7.71 (s, 1H), 7.58 (m, 2H), 7.41 (m, 1H), 5.12 (bs, 1H), 4.75 (AB, 2H), 4.20 (m, 1H), 3.10 (dd, 1H), 2.89 (dd, 1H), 1.45 (s, 9H).

C. 3-(3-(S)-amino-2,5-dioxo-pyrrolidin-1-ylmethyl)-benzonitrile hydrochloride.

The title compound is prepared as in EXAMPLE 1, Part C using 1-(3-cyanobenzyl)-2,5-dioxo-pyrrolidin-3-(S)-yl]-carbamic acid tert-butyl ester as the starting material.

$^1$H NMR (DMSO-d$_6$, 300 MHz) d 8.85 (bs, 2H), 7.60 (m, 4H), 4.68 (AB, 2H), 4.45 (m, 1H), 3.12 (dd, 1H), 2.80 (dd, 1H).

D. 7-Methoxynaphthalene-2-sulfonic acid [1-(3-cyanobenzyl)-2,5-dioxo-pyrolidin-3-(S)-yl]-amide.

The title compound is prepared as in EXAMPLE 1, Part D using 3-(3-(S)-amino-2,5-dioxo-pyrrolidin-1-ylmethyl)-benzonitrile hydrochloride and 7-methoxynaphthalene-2-sulfonyl chloride.

$^1$H NMR (CDCl$_3$, 300 MHz) d 8.31 (s, 1H), 7.91 (d, 1H), 7.81 (d, 1H), 7.70 (d, 1H), 7.56 (m, 2H), 7.35 (m, 2H), 7.21 (m, 2H), 5.39 (bs, 1H), 4.62 (AB, 2H), 4.12 (m, 1H), 3.92 (s, 3H), 3.15 (dd, 1H), 2.90 (dd, 1H).

E. 7-Methoxynaphthalene-2-sulfonic acid {1-[3-(aminoiminomethyl)-benzyl]-2,5-dioxo-pyrrolidin-3-(S)-yl}-amide trifluoroactetate.

The title compound is prepared as in EXAMPLE 1, Part E using 7-methoxynaphthalene-2-sulfonic acid [1-(3-cyanobenzyl)-2,5-dioxo-pyrrolidin-3-(S)-yl]-amide as the starting material.

$^1$H NMR (DMSO-d$_6$, 300 MHz) d 9.29 (bs, 2H), 9.18 (bs, 2H), 8.42 (d, 1H), 8.39 (s, 1H), 8.05 (d, 1H), 7.95 (d, 1H), 7.70 (m, 3H), 7.48 (m, 3H), 7.37 (d, 1H), 4.68 (m, 3H), 3.89 (s, 3H), 2.80 (dd, 1H), 2.32 (dd, 1 H) FAB MS, [M+H]$^+$= 467. Elemental analysis calculated with 1.75 mole of H$_2$O: C=49.06%, H=4.36%, N=9.15%, found C=48.99%, H=4.17%, N=8.98%.

EXAMPLE 20

Naphthalene-2-sulfonic acid {1-[3-(aminoiminomethyl)-benzyl]-2-oxo-piperidin-3-yl}-amide trifluoroacetate.

A. 3-[N-Boc)-3-amino-2-oxo-piperidin-1-ylmethyl]-benzonitrile.

A mixture of N-a-Boc-L-ornithine (1.50 g, 6.45 mmol) and 3-cyanobenzaldehyde (0.42 g, 3.23 mmol) are suspended in 20 mL of MeOH. A solution of anhydrous zinc chloride (0.24 g, 1.79 mmol) and sodium cyanoborohydride (0.22 g, 3.5 mmol) in 5 mL of MeOH is added. The mixture is stirred for 16 hours at room temperature. After this time, 20 mL of 1N NaOH is added. The solution is concentrated and the residue is partitioned between EtOAc and water. The organic layer is washed with saturated NaCl. The organic layer is dried over MgSO₄, filtered and concentrated to give N-a-Boc-N-d-(3-cyanobenzyl)-L-ornithine. A portion of the crude residue (0.5 g, 2.16 mmol), BOP reagent (1.05 g, 2.38 mmol) and potassium hydrogen carbonate (1.08 g, 10.8 mmol) are dissolved in 20 mL of DMF. The reaction mixture is stirred for 16 hours and then diluted with 300 mL of EtOAc. The organic layer is washed with 1N HCl, 10% Na₂CO₃ and saturated NaCl. The organic layer is dried over MgSO₄, filtered and concentrated. The residue is purified by column chromatography eluting with a gradient of 15% EtOAc/CH₂Cl₂ to 35% EtOAc/CH₂Cl₂ to give the title compound (0.26 g, 0.76 mmol) as a solid.

$^1$H NMR (CDCl₃, 300 MHz) d 7.49 (m, 4H), 5.50 (bs, 1H), 4.59 (s, 2H), 4.08 (m, 1H), 3.21 (m, 2H), 2.48 (m, 1H), 1.89 (m, 2H), 1.62 (m, 1H), 1.45 (s, 9H.

B Naphthalene-2-sulfonic acid [1-(3-cyanobenzyl)-2-oxo-piperidin-3-yl]amide.

3-[(N-Boc)-3-amino-2-oxo-piperidin-1-ylmethyl]-benzonitrile (0.25 g, 0.76 mmol) is dissolved in 5 mL of CH₂Cl₂. To the solution is added 1.0 mL of trifluoroacetic acid. The mixture is stirred for 3 hours at room temperature and then concentrated. The residue is reconcentrated from toluene to give 3-(3-amino-2-oxo-piperidin-1-ylmethyl)-benzonitrile trifluoroacetate (0.23 g, 0.76 mmol) as a solid. The crude product is then treated as in EXAMPLE 1, Part D to give the title compound.

$^1$H NMR (CDCl₃, 300 MHz) d 8.49 (s, 1H), 7.94 (m, 4H), 7.51 (m, 6H), 6.10 (s, 1H), 4.47 (AB, 2H), 3.56 (m, 1H), 3.20 (m, 2H), 2.52 (m, 1H), 1.83 (m, 3H).

C. Naphthalene-2-sulfonic acid {1-[3-(aminoiminomethyl)-benzyl]-2-oxo-piperidin-3-yl}-amide trifluoroacetate.

The title compound is prepared as in EXAMPLE 1, Part E using naphthalene-2sulfonic acid [1-(3-cyanobenzyl)-2-oxo-piperidin-3-yl]-amide as the starting material.

$^1$H NMR (DMSO-d₆, 300 MHz) d 9.29 (bs, 2H), 9.19 (bs, 2H), 8.48 (s, 1H), 8.04 (m, 4H), 7.90 (d, 1H), 7.60 (m, 6H), 4.48 (s, 2H), 3.95 (m, 1H), 3.18 (s, 2H), 1.86 (m, 1H), 1.69 (m, 3H). FAB MS, [M+H]⁺=437. Elemental analysis calculated with 1.0 mole of H₂O: C=52.81%, H=4.79%, N=9.84%, found C=52.85%, H=4.77%, N=9.15%.

EXAMPLE 21

7-Methoxynaphthalene-2-sulfonic acid {1-[3-(aminoiminomethyl)-benzyl]-2-oxo-azepan-3-(S)-yl}-amide trifluoroacetate.

A. L-(-)-a-BOC-amino-e-caprolactam.

L-(-)-a-Amino-e-caprolactam (5.0 g, 39 mmol) and triethylamine (4.9 g, 49 mmol) are dissolved in 100 mL of CH₂Cl₂. To the solution is added Boc anhydride (8.5 g, 39 mmol) and dimethylaminopyridine (0.1 g). The reaction mixture is stirred for 16 hours at room temperature. After this time, the solution is washed with 1N HCl, 10% Na₂CO₃ and saturated NaCl. The organic layer is dried over MgSO₄, filtered and concentrated to give the title compound (6.23 g, 27 mmol) as a solid.

$^1$H NMR (CDCl₃, 300 MHz) d 6.15 (bs, 1H), 5.90 (bs, 1H), 4.24 (m, 1H), 3.21 (m, 2H), 2.05 (m, 2H), 1.79 (m, 2H), 1.45 (m, 11H).

B. [1-(3-Cyanobenzyl)-2-oxo-azepan-3-(S)-yl]-carbamic acid tert-butyl ester.

L-(-)-a-Boc-amino-e-caprolactam (1.07 g, 4.7 mmol) is dissolved in 45 mL of THF and cooled to 0° C. To the solution is added a 1M solution of lithium hexamethyldisilylazide (4.7 mL, 4.7 mmol) in THF. The mixture is stirred for 30 min at 0° C. To the resulting solution is added a-bromo-m-tolunitrile (0.90 g, 4.7 mmol). The reaction mixture is stirred for 4 hours. The solution is diluted with 100 mL of EtOAc and is washed with 1N HCl, 10% Na₂CO₃ and saturated NaCl. The organic layer is dried over MgSO₄, filtered and concentrated. The residue is purified by column chromatography eluting with 20% EtOAc/CH₂Cl₂ to give the title compound (1.05 g, 3.1 mmol) as a solid.

$^1$H NMR (CDCl₃, 300 MHz) d 7.45 (m, 4H), 5.95 (d, 1H), 4.85 (AB, 1H), 4.35 (AB, 1H), 4.40 (m, 1H), 3.48 (m, 1H), 3.15 (dd, 1H), 2.05 (m, 1H), 1.90 (m, 1H), 1.70 (m, 2H), 1.49 (m, 1H), 1.45 (s, 9H), 1.20 (m, 1H).

C. 3-(3-(S)-Amino-2-oxo-azepan-1-ylmethyl)-benzonitrile hydrochloride.

The title compound is prepared as in EXAMPLE 1, Part C using [1-(3-cyanobenzyl)-2-oxo-azepan-3-(S)-yl]-carbamic acid tert-butyl ester as the starting material. EI MS, [M]⁺=243.

D. 7-Methoxynaphthalene-2-sulfonic acid [1-(3-cyanobenzyl)-2-oxo-azepan-3-(S)-yl]-amide.

The title compound is prepared as in EXAMPLE 1, Part D using 3-(3-(S)-amino-2-oxo-azepan-1-ylmethyl)-benzonitrile hydrochloride and 7-methoxynaphthalene sulfonyl chloride as the starting materials.

$^1$H NMR (CDCl₃, 300 MHz) d 8.32 (s, 1H), 7.88 (m, 2H), 7.68 (d, 1H), 7.29 (m, 3H), 7.08 (m, 1H), 6.96 (m, 1H), 6.35 (d, 1H), 4.80 (AB, 1H), 4.10 (AB, 1H), 4.00 (m, 1H), 3.92 (s, 3H), 3.19 (m, 1H), 3.05 (m, 1H), 2.18 (m, 1H), 1.95 (m, 1H), 1.65 (m, 2H), 1.18 (m, 3H).

E. 7-Methoxynaphthalene-2-sulfonic acid {1-[3-(aminoiminomethyl)-benzyl]-2-oxo-azepan-3-(S)-yl}-amide trifluoroacetate.

The title compound is prepared as in EXAMPLE 1, Part E using 7-methoxy naphthalene-2-sulfonic acid [1-(3-cyanobenzyl)-2-oxo-azepan-3-(S)-yl]-amide as the starting material.

$^1$H NMR (DMSO-d₆, 300 MHz) d 9.28 (bs, 2H), 9.08 (bs, 2H), 8.32 (s, 1H), 7.95 (m, 2H), 7.79 (d, 1H), 7.62 (m, 3H), 7.60 (d, 1H), 7.32 (m, 2H), 7.10 (d, 1H), 4.13 (AB, 2H), 3.89 (s, 3H), 3.40 (m, 1H), 3.15 (m, 1H), 1.79 (m, 3H), 1.51 (m, 3H), 1.12 (m, 1H). FAB MS, [M+H]⁺=481. Elemental analysis calculated with 0.5 mole of H₂O: C=53.73%, H=5.01%, N=9.28%, found C=53.77%,.H=4.86%, N=9.26%.

EXAMPLE 22

7-Methoxy-naphthalene-2-sulfonic acid {1-[3-(aminoiminomethyl)-benzyl]-2-oxo-pyrrolidin-3-(S)-yl}methyl amide trifluoroacetate.

A. 7-Methoxy-naphthalene-2-sulfonic acid [1-(3-cyanobenzyl)-2-oxo-pyrrolidin-3-(S)-yl]methyl amide.

The title compound is prepared as in EXAMPLE 17, Part A using 7-methoxy-naphthalene-2-sulfonic acid [1-(3-cyanobenzyl)-2-oxo-pyrrolidin-3-(S)-yl]-amide as the starting material.

$^1$H NMR (CDCl₃, 300 MHz) d 8.44 (d, 1H), 7.92 (d, 1H), 7.82 (m, 2H), 7.61 (m, 1H), 7.47 (m, 3H), 7.28 (m, 2H), 4.97 (m, 1H), 4.53 (AB, 1H), 4.39 (AB, 1H), 3.96 (s, 3H), 3.13 (m, 2H), 2.83 (s, 3H), 2.36 (m, 1H), 2.37 (m, 1H), 2.06 (m, 1H).

B. 7-Methoxy-naphthalene-2-sulfonic acid {1-[3-(aminoiminomethyl)-benzyl]-2-oxo-pyrrolidin-3-(S)-yl}methyl amide trifluoroacetate.

The title compound is prepared as described in EXAMPLE 1, Part E using 7-Methoxy-naphthalene-2-sulfonic acid [1-(3-cyanobenzyl)-2-oxo-pyrrolidin-3-(S)-yl] methyl amide as the starting material.

$^1$H NMR (DMSO-d$_6$, 300 MHz) d 9.28 (bs, 2H), 9.07 (bs, 2H), 8.38 (s, 1H), 8.01 (d, 1H), 7.93 (s, 1H), 7.68 (m, 2H), 7.54 (m, 4H), 7.33 (d, 1H), 4.90 (m, 1H), 4.40 (AB, 2H), 3.88 (s, 3H), 3.12 (m, 2H), 2.66 (s, 3H), 1.98 (m, 1H), 1.75 (m, 1H). FAB MS, [M+H]$^+$=467. Elemental analysis calculated with 2.5 mole of H$_2$O: C=49.92%, H=5.16%, N=8.96%, found C=50.03%, H=4.56%, N=8.70%.

Other compounds prepared according to the the procedures above include those encompassed by the following formula:

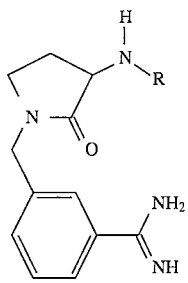

wherein R is

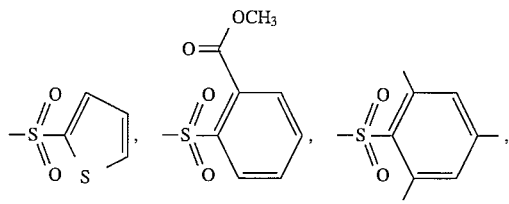

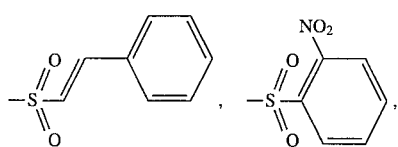

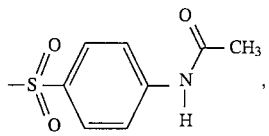

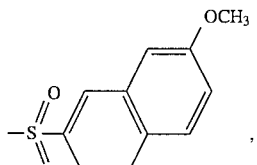

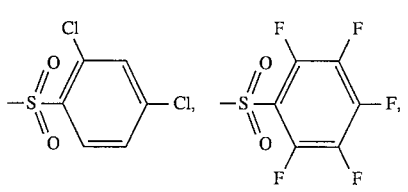

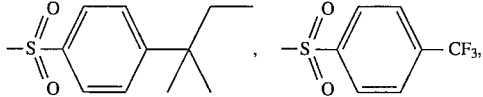

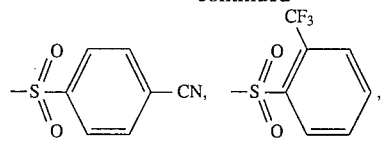

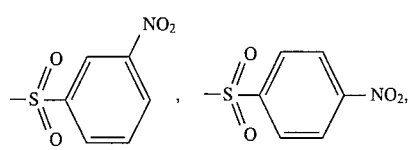

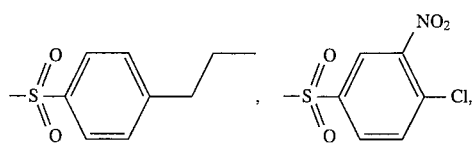

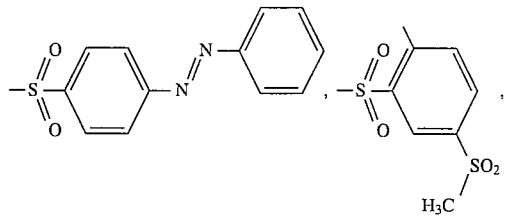

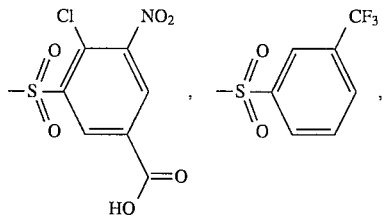

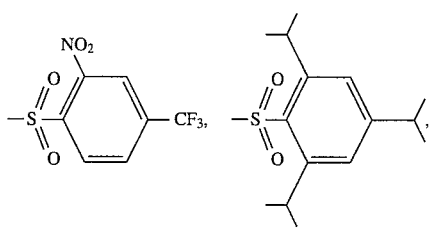

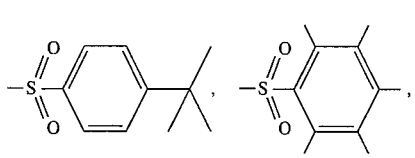

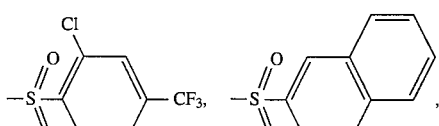

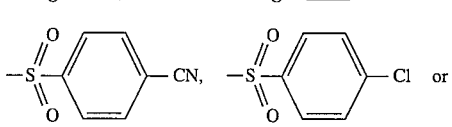

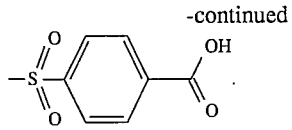

The molecules described herein inhibit blood coagulation by virtue of their ability to inhibit the penultimate enzyme in the coagulation cascade, factor Xa, rather than thrombin. Both free factor Xa and factor Xa assembled in the prothrombinase complex (Factor Xa, Factor Va, calcium and phospholipid) are inhibited. Factor Xa inhibition is obtained by direct complex formation between the inhibitor and the enzyme and is therefore independent of the plasma co-factor antithrombin III. Effective factor Xa inhibition is achieved by administering the compounds either by oral administration, continuous intravenous infusion, bolus intravenous administration or any other parenteral route such that it achieves the desired effect of preventing the factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening thrombin throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

These compounds may be used alone or in combination with other diagnostic, anticoagulant, antiplatelet or fibrinolytic agents. For example adjunctive administration of factor Xa inhibitors with standard heparin, low molecular weight heparin, direct thrombin inhibitors (i.e. hirudin), aspirin, fibrinogen receptor antagonists, streptokinase, urokinase and/or tissue plasminogen activator may result in greater antithrombotic or thrombolytic efficacy or efficiency. The compounds described herein may be administered to treat thrombotic complications in a variety of animals such as primates including humans, sheep, horses, cattle, pigs, dogs, rats and mice. Inhibition of factor Xa is useful not only in the anticoagulant therapy of individuals having thrombotic conditions but is useful whenever inhibition of blood coagulation is required such as to prevent coagulation of stored whole blood and to prevent coagulation in other biological samples for testing or storage. Thus, any factor Xa inhibitor can be added to or contacted with any medium containing or suspected of containing factor Xa and in which it is desired that blood coagulation be inhibited.

In addition to their use in anticoagulant therapy, factor Xa inhibitors may find utility in the treatment or prevention of other diseases in which the generation of thrombin has been implicated as playing a pathologic role. For example, thrombin has been proposed to contribute to the morbidity and mortality of such chronic and degenerative diseases as arthritis, cancer, atherosclerosis and Alzheimer's disease by virtue of its ability to regulate many different cell types through specific cleavage and activation of a cell surface thrombin receptor. Inhibition of factor Xa will effectively block thrombin generation and therefore neutralize any pathologic effects of thrombin on various cell types.

According to a further feature of the invention there is provided a method for the treatment of a human or animal patient suffering from, or subject to, conditions which can be ameliorated by the administration of an inhibitor of Factor Xa, for example conditions as hereinbefore described, which comprises the administration to the patient of an effective amount of compound of formula I or a composition containing a compound of formula I. "Effective amount" is meant to describe an amount of compound of the present invention effective in inhibiting Factor Xa and thus producing the desired therapeutic effect.

The present invention also includes within its scope pharmaceutical formulations which comprise at least one of the compounds of formula I in association with a pharmaceutically acceptable carrier or coating.

In practice compounds of the present invention may generally be administered parenterally, intravenously, subcutaneously intramuscularly, colonically, nasally, intraperitoneally, rectally or orally.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed Onto a suitable solid carrier for use in a dry powder inhaler.

Solid compositions for rectal administration include suppositories formulated in accordance with known methods and containing at least one compound of formula I.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100, preferably about 0.01 to about 10, mg/kg body weight per day by inhalation, from about 0.01 to about 100, preferably 0.1 to 70, more especially 0.5 to 10, mg/kg body weight per day by oral administration, and from about 0.01 to about 50, preferably 0.01 to 10, mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

Compounds within the scope of the present invention exhibit marked pharmacological activities according to tests described in the literature which tests results are believed to correlate to pharmacological activity in humans and other mammals. The following pharmacological test results are typical characteristics of compounds of the present invention.

Factor Xa Inhibitor Patents: Enzyme Assay Methods

Please find below a section describing the methods used for evaluating the activity of the compounds used in the factor Xa program for insertion into the patent.

Enzyme Assays:

The ability of the compounds in the present invention to act as catalytic inhibitors of factor Xa, thrombin, trypsin, tissue-plasminogen activator (t-PA), urokinase-plasminogen activator (u-PA), plasmin and activated protein C was evaluated by determining the concentration of inhibitor which resulted in a 50% loss in enzyme activity (IC50) using purified enzymes.

All enzyme assays were carried out at room temperature in 96-well microtiter plates using a final enzyme concentration of 1 nM. The concentrations of factor Xa and thrombin were determined by active site titration and the concentrations of all other enzymes were based on the protein concentration supplied by the manufacturer The respective buffers, substrates and substrate concentrations used in each enzyme assay are outlined in the table below. Compounds were dissolved in DMSO, diluted with their respective buffers and assayed at a maximal final DMSO concentration of 1.25%. Compound dilutions were added to wells containing buffer and enzyme and pre-equilibrated for between 5 and 30 minutes. The enzyme reactions were initiated by the addition of substrate and the color developed from the hydrolysis of the peptide-p-nitroanilide substrates was monitored continuously for 5 minutes at 405 nm on a Vmax microplate reader (Molecular Devices). Under these conditions, less than 10% of the substrate was utilized in all assays. The initial velocities measured were used to calculate the amount of inhibitor which resulted in a 50% reduction of the control velocity (IC50). The apparent Ki values were then determined according to the Cheng-Prusoff equation (IC50=Ki[I+[S]/Km]) assuming competitive inhibition kinetics.

The following Composition Examples illustrate pharmaceutical compositions according to the present invention.

COMPOSITION EXAMPLE 1

N-(2,6-Difluorophenyl)-3ocyclopentyloxy-4-methoxybenzamide (1 g) (mean particle size 3.5 microns) and lactose (99 g) (mean particle size 72 microns) were blended together for 30 minutes in a mechanical shaker/mixer. The resulting blend was filled to a fill weight of 25 mg, into No. 3 hard gelatin capsules, to give a product suitable for use, for example, with a dry powder inhaler.

COMPOSITION EXAMPLE 2

N-(3,5-Dichloropyrid-4-yl)-3-cyclopentyloxy-4-methoxybenzamide (1 g) (mean particle size 3.5 microns) and lactose (99 g) (mean particle size 72 microns) are blended together for 30 minutes in a mechanical shaker/mixer. The resulting blend is filled, to a fill weight of 25 mg, into No. 3 hard gelatin capsules, to give a product suitable for use, for example, with a dry powder inhaler.

COMPOSITION EXAMPLE 3

No. 2 size gelatin capsules each containing:-

| | |
|---|---|
| N-(3,5-dichloropyrid-4-yl)-3-cyclopentyloxy-4-methoxybenzamide | 20 mg |
| lactose | 100 mg |
| starch | 60 mg |
| dextrin | 40 mg |
| magnesium stearate | 1 mg | are prepared in accordance with the usual procedure.

The present invention may be embodied in other specific forms without departing from the spirit or essential attributes thereof.

What is claimed is:

1. A compound of formula I

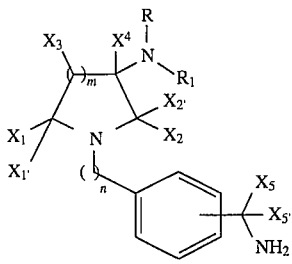

X$_1$ and X$_{1'}$ are hydrogen;

X$_2$ and X$_{2'}$ are independently selected from the group of hydrogen, alkyl, aryl, aralkyl, carboxyalkyl, alkoxycarbonylalkyl or hydroxyalkyl, or X$_1$ and X$_{1'}$ or X$_2$ and X$_{2'}$ independently taken together form oxo;

X$_3$ is hydroxy, alkyl, aralkyl or aryl, or X$_3$ and one of X$_1$ and X$_{1'}$ taken together form a 4 to 7 membered ring;

X$_4$ is hydrogen, alkyl, aralkyl, or hydroxyalkyl;

X$_5$ and X$_{5'}$ are hydrogen or taken together are =NH;

m is 1, 2 or 3;

n is 1, 2 or 3;

R is hydrogen, alkyl, alkylaryl, hydroxyalkyl or alkoxy;

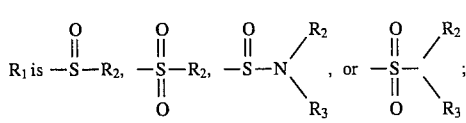

R$_2$ is alkyl, aralkyl, cycloalkyl, aryl, substituted aryl, heteroaryl, substituted heteroaryl, hetereocyclyl, or R and R$_2$ taken together form a 5 to 7 membered ring; and R$_3$ is alkyl, cycloalkyl or aryl, or R$_2$ and R$_3$ taken together form a 4 to 7 membered ring, or a pharmaceutically acceptable salt thereof, an N-oxide thereof, a hydrate thereof or a solvate thereof.

2. The compound of claim 1 wherein R$_2$ is biphenyl, substituted biphenyl, naphthyl or substituted naphthyl.

3. The compound of claim 1 wherein n is 1.

4. The compound of claim 1 wherein X$_2$ and X$_{2'}$ take together form oxo.

5. The compound of claim 1 wherein X$_1$, X$_{1'}$, X$_3$ and X$_4$ are hydrogen.

6. The compound of claim 1 wherein X$_5$ is hydrogen or alkyl.

7. The compound of claim 1 wherein aminoiminomethyl on the N-phenylalkyl is in the meta position.

8. The compound of claim 1 wherein X$_1$ is hydrogen and X$_{1'}$ is carboxyalkyl, alkoxycarbonylalkyl or aryl, or X$_1$ and X$_{1'}$ taken together form oxo.

9. The compound of claim 1 wherein R$_1$ is SO$_2$R$_2$.

10. A compound according to claim 1 which is

Naphthalene-2-sulfonic acid {1-[3-(aminoiminomethyl)-benzyl]-2-oxo-pyrrolidin-3-(S)-yl}-amide trifluoroacetate;

Dibenzofuran-2-sulfonic acid {1-[3-(aminoiminomethyl)-benzyl]-5-oxo-pyrrolidin-3-yl}-amide trifluoroacetate;

Toluene-4-sulfonic acid {1-[3-(aminoiminomethyl)-benzyl]-2-oxo-pyrrolidin-3-(S)-yl}-amide trifluoroacetate;

3,4-Dihydro-1H-isoquinoline-2-sulfonic acid {1-[3-(aminoiminomethyl)-benzyl]-2-oxo-pyrrolidin-3-(S)-yl}-amide trifluoroacetate;

3'-Methoxy-biphenyl-4-sulfonic acid {1-[3-(aminoiminomethyl)-benzyl]-2-oxo-pyrrolidin-3-(S)-yl}-amide trifluoroacetate;

Naphthalene-1-sulfonic acid {1-[3-(aminoiminomethyl)-benzyl]-2-oxo-pyrrolidin-3-(S)-yl}-amide trifluoroacetate;

5-Pyrid-2-yl-thiophene-2-sulfonic acid {1-[3-(aminoiminomethyl)-benzyl]-2-oxo-pyrrolidin-3-(S)-yl}-amide trifluoroacetate;

Biphenyl-4-sulfonic acid {1-[3-(aminoiminomethyl)-benzyl]-2-oxo-pyrrolidin-3-(S)-yl}-amide trifluoroacetate;

7-Methoxynaphthalene-2-sulfonic acid {1-[3-(aminoiminomethyl)-benzyl]-2-oxo-pyrrolidin-3-(S)-yl}-amide trifluoroacetate;

7-Ethoxynaphthalene-2-sulfonic acid {1-[3-(aminoiminomethyl)-benzyl]-2-oxo-pyrrolidin-3-(S)-yl}-amide trifluoroacetate;

5-Chloro-6-methoxynaphthalene-2-sulfonic acid {1-[3-(aminoiminomethyl)-benzyl]-2-oxo-pyrrolidin-3-(S)-yl}-amide trifluoroacetate;

5-Chloro-6,7-dimethoxynaphthalene-2-sulfonic acid {1-[3-(aminoiminomethyl)-benzyl]-2-oxo-pyrrolidin-3-(S)-yl}-amide trifluoroacetate;

5-Chloro-6,7-dimethoxynaphthalene-2-sulfonic acid {1-[3-(aminoiminomethyl)-benzyl]-2-oxo-pyrrolidin-3-(S)-yl}-amide trifluoroacetate;

7-Aminonaphthalene-2-sulfonic acid {1-[3-(aminoiminomethyl)-benzyl]-2-oxo-pyrrolidin-3-(S)-yl}-amide ditrifluoroacetate;

Naphthalene-2-sulfonic acid {1-[4-(aminoiminomethyl)-benzyl]-2-oxo-pyrrolidin-3-(S)-yl}-amide trifluoroacetate;

7-Methoxynaphthalene-2-sulfonic acid [1-(3-aminomethyl-benzyl)-2-oxo-pyrrolidin-3-(S)-yl]-amide trifluoroacetate;

Naphthalene-2-sulfonic acid {1-[3-(aminoiminomethyl)-benzyl]-2-oxo-pyrrolidin-3-(S)-yl}methyl amide trifluoroacetate;

Naphthalene-2-sulfonic acid {1-[3-(aminoiminomethyl)-benzyl]-pyrrolidin-3-(S)-yl}-amide ditrifluoroacetate;

7-Methoxynaphthalene-2-sulfonic acid {1-[3-(aminoiminomethyl)-benzyl]-2,5-dioxo-pyrrolidin-3-(S)-yl}-amide trifluoroacetate;

Naphthalene-2-sulfonic acid {1-[3-(aminoiminomethyl)-benzyl]-2-oxo-piperidin-3-yl}-amide trifluoroacetate;

7-Methoxynaphthalene-2-sulfonic acid {1-[3-(aminoiminomethyl)-benzyl]-2-oxo-azepan-3-(S)-yl}-amide trifluoroacetate; or 7-Methoxy-naphthalene-2-sulfonic acid {1-[3-(aminoiminomethyl)-benzyl]-2-oxo-pyrrolidin-3-(S)-yl}methyl amide trifluoroacetate.

11. A pharmaceutical composition comprising the compound according to claim 1 and a pharmaceutically acceptable carrier.

12. A method for treating a patient suffering from a condition capable of being modulated by inhibiting an activity of Factor Xa by administering a therapeutically effective amount of the compound according to claim 1.

* * * * *

UNITED STATES PATENT AND TRADEMARK OFFICE
CERTIFICATE OF CORRECTION

PATENT NO. : 5,612,353
DATED : March 18, 1997
INVENTOR(S) : William R. Ewing et al.

It is certified that error appears in the above-identified patent and that said Letters Patent is hereby corrected as shown below:

At column 2, line 31, please delete " 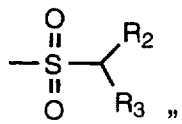 " and insert -- 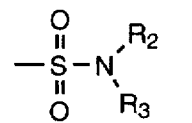 -- therefor.

At column 4, line 8, please delete "naphthlenemethyl" and insert --naphthalenemethyl-- therefor.

At column 6, lines 4-6, please delete "5-Chloro-6,7-dimethoxynaphthalene-2-sulfonic acid {1-[3-(aminoiminomethyl)-benzyl]-2-oxo-pyrrolidin-3-(S)-yl}-amide trifluoroacetate" and insert --Dibenzofuran-2-sulfonic acid {1-[3-(aminoiminomethyl)-benzyl]-2-oxo-pyrrolidin-3-(S)-yl}-amide trifluoroacetate-- therefor.

At column 7, lines 4-6, please delete "5-Chloro-6,7-dimethoxynaphthalene-2-sulfonic acid {1-[3-(aminoiminomethyl)-benzyl]-2-oxo-pyrrolidin-3-(S)-yl}-amide trifluoroacetate" and insert -- Dibenzofuran-2-sulfonic acid {1-[3-(aminoiminomethyl)-benzyl]-2-oxo-pyrrolidin-3-(S)-yl}-amide trifluoroacetate-- therefor.

At column 8, line 12, please delete "cataytic" and insert --catalytic-- therefor; line 48, please delete "atolls" and insert --atoms-- therefor.

UNITED STATES PATENT AND TRADEMARK OFFICE
CERTIFICATE OF CORRECTION

PATENT NO. : 5,612,353
DATED : March 18, 1997
INVENTOR(S) : William R. Ewing et al.

It is certified that error appears in the above-identified patent and that said Letters Patent is hereby corrected as shown below:

At column 14, line 4, please delete "minutes" and insert --minute-- therefor.

At column 16, line 5, please delete "$_{300}$ MHz" and insert --300 MHz-- therefor.

At column 17, line 26, please delete "7.62 (s, 1H)".

At column 19, lines 44-45, please delete "Biphenyl-4sulfonic acid [1-(3-cyanobenzyl)-2-oxo-pyrrolidin-3-(S)-yl]-amide" and insert --Biphenyl-4-sulfonic acid [1-(3-cyanobenzyl)-2-oxo-pyrrolidin-3-(S)-yl]-amide-- therefor;
    lines 56-58, please delete "Biphenyl-4-8-sulfonic acid {1-[3-(aminoiminomethyl)-benzyl]-2-oxo-pyrrolidin-3-(S)-yl}-amide trifluoroacetate" and insert --Biphenyl-4-sulfonic acid {1-[3-(aminoiminomethyl)-benzyl]-2-oxo-pyrrolidin-3-(S)-yl}-amide trifluoroacetate-- therefor.

At column 22, lines 22-24, please delete "5-Chloro-6-metboxynaphthalene-2-sulfonic acid {1-[3-(aminoiminomethyl)-benzyl]-2-oxo-pyrrolidin-3-(S)-yl}-amide trifluoroacetate" and insert --5-Chloro-6-methoxynaphthalene-2-sulfonic acid {1-[3-(aminoiminomethyl)-benzyl]-2-oxo-pyrrolidin-3-(S)-yl}-amide trifluoroacetate-- therefor;
    lines 35-36, please delete "5-chloro-6-methoxynaphthalene-2-sulfonic acid [1-(3-Cyanobenzyl)-2-oxo-pyrrolidin-3-(S)-yl]-amide" and insert --5-Chloro-6-methoxynaphthalene-2-sulfonic acid [1-(3-cyanobenzyl)-2-oxo-pyrrolidin-3-(S)-yl]-amide-- therefor.

At column 24, line 53, please delete "EtOAc/CH$_2$CL$_2$" and insert --EtOAc/CH$_2$Cl$_2$-- therefor;
    line 54, please delete "EtOAc/CH$_2$CL$_2$" and insert --EtOAc/CH$_2$Cl$_2$-- therefor.

UNITED STATES PATENT AND TRADEMARK OFFICE
CERTIFICATE OF CORRECTION

PATENT NO. : 5,612,353
DATED : March 18, 1997
INVENTOR(S) : William R. Ewing et al.

It is certified that error appears in the above-identified patent and that said Letters Patent is hereby corrected as shown below:

At column 26, line 7, please delete "NH3/MeOH" and insert --$NH_3$/MeOH-- therefor.

At column 27, line 25, please delete "a-Bromo-m-tolunitrile" and insert --α-Bromo-m-tolunitrile-- therefor;

lines 53-55, please delete "7-Methoxynaphthalene-2-sulfonic acid {1-[3-(aminoiminomethyl)-benzyl]-2.5-dioxo-pyrrolidin-3-(S)-yl}-amide trifluoroacetate" and insert --7-Methoxynaphthalene-2-sulfonic acid {1-[3-(aminoiminomethyl)-benzyl]-2,5-dioxo-pyrrolidin-3-(S)-yl}-amide trifluoroacetate-- therefor.

At column 28, line 9, please delete "Stirred" and insert --stirred-- therefor;

line 59, please delete "N-a-Boc-L-omithine" and insert --N-α-Boc-L-ornithine-- therefor.

At column 29, line 2, please delete "N-a-Boc-N-d-(3-cyanobenzyl)-L-omithine" and insert --N-α-Boc-N-δ-(3-cyanobenzyl)-L-ornithine-- therefor;

line 47, please delete "L-(-)-a-Boc-amino-e-caprolactam" and insert --L-(-)-α-Boc-amino-ε-caprolactam-- therefor;

line 48, please delete "L-(-)-a-Amino-e-caprolactam" and insert --L-(-)-α-Amino-ε-caprolactam-- therefor;

line 63, please delete "L-(-)-a-Boc-amino-e-caprolactam" and insert --L-(-)-α-Boc-amino-ε-caprolactam-- therefor.

UNITED STATES PATENT AND TRADEMARK OFFICE
CERTIFICATE OF CORRECTION

PATENT NO. : 5,612,353
DATED : March 18, 1997
INVENTOR(S) : William R. Ewing et al.

It is certified that error appears in the above-identified patent and that said Letters Patent is hereby corrected as shown below:

At column 30, line 1, please delete "a-bromo-m-tolunitrile" and insert --α-bromo-m-tolunitrile-- therefor.

At column 35, line 60, please delete "Patents".

At column 36, line 34, please delete "N-(2,6-Difluorophenyl)-3ocyclopentyloxy-4-methoxybenzamide" and insert --N-(2,6-Difluorophenyl)-3-cyclopentyloxy-4-methoxybenzamide-- therefor.

At column 37, line 30, please delete "  " and insert --  -- therefor.

At column 38, lines 25-27, please delete "5-Chloro-6,7-dimethoxynaphthalene-2-sulfonic acid {1-[3-(aminoiminomethyl)-benzyl]-2-oxo-pyrrolidin-3-(S)-yl}-amide trifluoroacetate" and insert --Dibenzofuran-2-sulfonic acid {1-[3-(aminoiminomethyl)-benzyl]-2-oxo-pyrrolidin-3-(S)-yl}-amide trifluoroacetate-- therefor.

Signed and Sealed this

Sixteenth Day of June, 1998

Attest:

BRUCE LEHMAN

Attesting Officer

Commissioner of Patents and Trademarks